US012569417B2

(12) United States Patent
Reynolds

(10) Patent No.: US 12,569,417 B2
(45) Date of Patent: Mar. 10, 2026

(54) COMPOSITIONS AND METHODS FOR PROMOTING MINERALIZATION

(71) Applicant: The University of Melbourne, Victoria (AU)

(72) Inventor: Eric Charles Reynolds, Victoria (AU)

(73) Assignee: The University of Melbourne, Victoria (AU)

( * ) Notice: Subject to any disclaimer, the term of this patent is extended or adjusted under 35 U.S.C. 154(b) by 958 days.

(21) Appl. No.: 17/438,272

(22) PCT Filed: Mar. 13, 2020

(86) PCT No.: PCT/AU2020/050236
§ 371 (c)(1),
(2) Date: Sep. 10, 2021

(87) PCT Pub. No.: WO2020/181334
PCT Pub. Date: Sep. 17, 2020

(65) Prior Publication Data
US 2022/0142881 A1 May 12, 2022

(30) Foreign Application Priority Data

Mar. 13, 2019 (AU) ................................ 2019900834
Oct. 14, 2019 (AU) ................................ 2019903859

(51) Int. Cl.
*A61K 8/24* (2006.01)
*A61Q 11/00* (2006.01)

(52) U.S. Cl.
CPC ................ *A61K 8/24* (2013.01); *A61Q 11/00* (2013.01)

(58) Field of Classification Search
CPC ................................... A61K 8/24; A61Q 11/00
See application file for complete search history.

(56) References Cited

U.S. PATENT DOCUMENTS

| | | |
|---|---|---|
| 3,864,471 A | 2/1975 | King et al. |
| 3,966,901 A | 6/1976 | Cullum et al. |
| 4,080,440 A | 3/1978 | Digiulio et al. |
| 4,157,386 A | 6/1979 | La Rochelle |
| 4,357,318 A | 11/1982 | Shah et al. |
| 4,522,805 A | 6/1985 | Gordon |
| 4,588,763 A | 5/1986 | Brannstrom et al. |
| 4,672,032 A | 6/1987 | Slavkin et al. |
| 5,015,628 A | 5/1991 | Reynolds |
| 5,227,154 A | 7/1993 | Reynolds |
| 5,427,769 A | 6/1995 | Berrocal et al. |
| 5,447,732 A | 9/1995 | Tanimoto et al. |
| 5,520,725 A | 5/1996 | Kato et al. |
| 5,833,953 A | 11/1998 | Berrocal et al. |
| 5,981,475 A | 11/1999 | Reynolds |
| 6,036,944 A | 3/2000 | Winston et al. |
| 6,056,930 A | 5/2000 | Tung |
| 6,120,754 A | 9/2000 | Lee et al. |
| 6,149,894 A | 11/2000 | Yamane et al. |
| 6,214,101 B1 | 4/2001 | Nakaseko |
| 6,652,875 B1 | 11/2003 | Bannister |
| 6,780,844 B1 | 8/2004 | Reynolds |
| 7,312,193 B2 | 12/2007 | Reynolds |
| 7,491,694 B2 | 2/2009 | Reynolds et al. |
| 8,354,117 B2 | 1/2013 | Tsunekawa et al. |
| 8,603,988 B2 | 12/2013 | Reynolds |
| 8,609,071 B2 | 12/2013 | Reynolds |
| 8,673,363 B2 | 3/2014 | Reynolds |
| 9,125,853 B2 | 9/2015 | Reynolds |

(Continued)

FOREIGN PATENT DOCUMENTS

| | | |
|---|---|---|
| AU | 718253 B2 | 7/1997 |
| CN | 104001157 A | 8/2014 |

(Continued)

OTHER PUBLICATIONS

A. L. Boskey* and A. S. Posner. "Conversion of Amorphous Calcium Phosphate to Microcrystalline Hydroxyapatite. A pH-Dependent, Solution-Mediated, Solid-Solid Conversion," The Journal of Physical Chemistry, vol. 77, No. 19, 1973, 2313-2317. (Year: 1973).*
U.S. Appl. No. 17/438,299, filed Sep. 10, 2021.
Madhavan, S et al., "Dentinal hypersensitivity: A comparative clinical evaluation of CPP-ACPF, sodium fluoride, propolis, and placebo", Journal of Conservative Dentistry, 2012; 15(4): 315-318.
P.J. Eke, et al. "Prevalence of Periodontitis in Adults in the United States: 2009 and 2010." J Dent Res 91:914-920 (2012). (Year: 2012).
Ajaj et al., "Effect of different acid etchants on the remineralization process of white-spot lesions: An in vitro study.", American Journal of Dentistry, Feb. 2020; pp. 43-47.

(Continued)

*Primary Examiner* — Michael P Cohen
(74) *Attorney, Agent, or Firm* — Foley & Lardner LLP

(57) ABSTRACT

The present invention relates to compositions for uses including mineralizing a dental surface, in particular tooth enamel. Methods of mineralizing hypomineralized lesions (including subsurface lesions) in the tooth enamel caused by various means including dental caries, dental corrosion and fluorosis are also provided. In one aspect, the present invention provides a method of mineralizing a dental surface or sub-surface comprising contacting the dental surface or subsurface with stabilized amorphous calcium phosphate (ACP) and/or amorphous calcium fluoride phosphate (ACFP), and simultaneously or subsequently, heating the dental surface or subsurface to which the stabilized ACP and/or ACFP has been, or is being, applied to a temperature greater than 37° C. In another aspect, the present invention provides a method of mineralizing a dental surface or sub-surface comprising contacting the dental surface or subsurface with a liquid composition comprising greater than 20% w/v stabilized amorphous calcium phosphate (ACP) and/or amorphous calcium fluoride phosphate (ACFP).

23 Claims, 3 Drawing Sheets
Specification includes a Sequence Listing.

(56) References Cited

U.S. PATENT DOCUMENTS

| | | | |
|---|---|---|---|
| 9,295,628 B2 | 3/2016 | Reynolds | |
| 9,668,945 B2 | 6/2017 | Reynolds | |
| 10,695,370 B2 | 6/2020 | Reynolds | |
| 10,912,722 B2 | 2/2021 | Reynolds | |
| 11,351,193 B2 | 6/2022 | Reynolds | |
| 11,504,305 B2 | 11/2022 | Reynolds | |
| 11,564,873 B2 | 1/2023 | Reynolds | |
| 11,717,536 B2 | 8/2023 | Reynolds | |
| 11,717,537 B2 | 8/2023 | Reynolds | |
| 12,128,068 B2 | 10/2024 | Reynolds | |
| 12,239,723 B2 | 3/2025 | Reynolds | |
| 2002/0028251 A1 | 3/2002 | Okay | |
| 2002/0071858 A1 | 6/2002 | Luo et al. | |
| 2003/0124066 A1 | 7/2003 | Dixon et al. | |
| 2003/0152525 A1 | 8/2003 | Dixon, Jr. et al. | |
| 2003/0165442 A1 | 9/2003 | Baig et al. | |
| 2005/0063922 A1 | 3/2005 | Reynolds et al. | |
| 2005/0089481 A1 | 4/2005 | Yamanaka et al. | |
| 2005/0100581 A1 | 5/2005 | Laurencin et al. | |
| 2005/0118115 A1 | 6/2005 | Fontenot | |
| 2006/0183081 A1 | 8/2006 | Bevilacqua et al. | |
| 2007/0071858 A1 | 3/2007 | Succar et al. | |
| 2007/0254260 A1 | 11/2007 | Alden et al. | |
| 2008/0075675 A1 | 3/2008 | Reynolds | |
| 2008/0171001 A1 | 7/2008 | Engelman et al. | |
| 2008/0193557 A1 | 8/2008 | Reynolds | |
| 2009/0016972 A1 | 1/2009 | Manasherov et al. | |
| 2009/0022672 A1 | 1/2009 | Reynolds | |
| 2009/0324662 A1 | 12/2009 | Kutsch et al. | |
| 2010/0028273 A1 | 2/2010 | Fischer et al. | |
| 2011/0076241 A1 | 3/2011 | Kato et al. | |
| 2012/0100194 A1 | 4/2012 | Yamai et al. | |
| 2012/0129135 A1 | 5/2012 | Yang et al. | |
| 2013/0129641 A1 | 5/2013 | Sadeghpour et al. | |
| 2014/0147512 A1 | 5/2014 | Reynolds | |
| 2016/0158283 A1 | 6/2016 | Reynolds | |
| 2017/0333296 A1 | 11/2017 | Reynolds | |
| 2018/0008518 A1 | 1/2018 | Reynolds | |
| 2020/0054672 A1 | 2/2020 | Reynolds | |
| 2020/0197486 A1 | 6/2020 | Reynolds | |
| 2020/0246378 A1 | 8/2020 | Reynolds | |
| 2021/0161778 A1 | 6/2021 | Reynolds | |
| 2022/0183810 A1 | 6/2022 | Reynolds | |
| 2023/0404867 A1 | 12/2023 | Reynolds | |
| 2024/0000671 A1 | 1/2024 | Reynolds | |
| 2024/0016836 A1 | 1/2024 | Reynolds | |
| 2025/0152482 A1 | 5/2025 | Reynolds | |
| 2025/0152666 A1 | 5/2025 | Reynolds | |

FOREIGN PATENT DOCUMENTS

| | | | |
|---|---|---|---|
| CN | 1040011574 A | 8/2014 | |
| EA | 011125 B1 | 12/2008 | |
| EP | 0 786 245 A1 | 7/1997 | |
| EP | 1 525 878 A1 | 4/2005 | |
| EP | 1 525 878 B1 | 3/2007 | |
| EP | 1 952 801 A1 | 8/2008 | |
| EP | 2 301 513 A2 | 3/2011 | |
| EP | 2 353 576 A1 | 8/2011 | |
| JP | H08-026925 A | 1/1996 | |
| JP | 08-143436 A | 6/1996 | |
| JP | H08-143436 A | 6/1996 | |
| JP | 10-290682 A | 11/1998 | |
| JP | H11-228327 A | 8/1999 | |
| JP | 11-310599 A | 11/1999 | |
| JP | 3742523 | 11/1999 | |
| JP | H11-310599 A | 11/1999 | |
| JP | 2002-338447 | 11/2002 | |
| JP | 2004-215521 A | 8/2004 | |
| JP | 2005-112841 A | 4/2005 | |
| JP | 2010-047494 A | 3/2010 | |
| JP | 2011-032250 A | 2/2011 | |
| JP | 2013-163656 A | 8/2013 | |
| WO | WO-82/03008 A1 | 9/1982 | |
| WO | WO-87/07615 | 12/1987 | |

| | | | | |
|---|---|---|---|---|
| WO | WO-93/03707 | 3/1993 | | |
| WO | WO-94/00146 A1 | 1/1994 | | |
| WO | WO-96/29340 A1 | 9/1996 | | |
| WO | WO-97/36943 A1 | 10/1997 | | |
| WO | WO-97/40811 A1 | 11/1997 | | |
| WO | WO 1998/40406 A1 | 9/1998 | | |
| WO | WO-9840406 A1 * | 9/1998 | ............ | A61K 33/42 |
| WO | WO-99/471089 | 9/1999 | | |
| WO | WO-00/06108 A1 | 2/2000 | | |
| WO | WO-00/57842 A1 | 10/2000 | | |
| WO | WO-00/57842 A2 | 10/2000 | | |
| WO | WO-00/57892 | 10/2000 | | |
| WO | WO-01/44106 A1 | 6/2001 | | |
| WO | WO-02/094204 A1 | 11/2002 | | |
| WO | WO-03/059303 A2 | 7/2003 | | |
| WO | WO-03/059304 A1 | 7/2003 | | |
| WO | WO-03/099234 | 12/2003 | | |
| WO | WO-2004/035077 A1 | 4/2004 | | |
| WO | WO-2004/054531 A1 | 7/2004 | | |
| WO | WO-2004/060336 A1 | 7/2004 | | |
| WO | WO-2006/056013 A1 | 6/2006 | | |
| WO | WO-2006/130913 A1 | 12/2006 | | |
| WO | WO-2006/135982 A1 | 12/2006 | | |
| WO | WO-2007/090242 A1 | 8/2007 | | |
| WO | WO-2009/099452 A1 | 8/2009 | | |
| WO | WO-2009/130447 A1 | 10/2009 | | |
| WO | WO-2010/134904 A1 | 11/2010 | | |
| WO | WO-2012/100991 A1 | 8/2012 | | |
| WO | WO-2013/117913 A2 | 8/2013 | | |
| WO | WO-2014/050144 | 4/2014 | | |
| WO | WO-2015010166 A1 * | 1/2015 | ............ | A61K 33/06 |
| WO | WO-2016/101041 A1 | 6/2016 | | |
| WO | WO-2018/165707 A1 | 9/2018 | | |
| WO | WO-2018/165708 A1 | 9/2018 | | |

OTHER PUBLICATIONS

Hsu C.-Y.S et al., "Laser-Matrix-Fluoride Effects on Enamel Demineralization", Journal of Dental Research, Sep. 2001; vol. 80, No. 9, pp. 1797-1801.

Huang et al., "Remineralisation Effect of CPP-ACP and Diode Laser Stabilised by Case on the Initial Enamel caries of Primary Teeth", Progress in Modern Biomedicine, Jan. 2019; 19(2): 279.

Kshirsagar et al., "Comparative assessment of bond strengths of affected dentin, using two different remineralizing solutions with or without lasers: Results of an in vitro pilot study", SRM Journal of Research in Dental Sciences, Jan. 2015; vol. 6, No. 2.

L.J. Walsh "Clinical applications of Recaldent products: which ones to use where," Australasian Dental Practice, May/Jun. 2007, 144-146. (Year: 2007).

Sakr, A. K., ELkarargy, A. A. M., & Sherif, M. M. (2007). The Effect of Recaldent (CPP-ACP) on the most putative bacteria in caries and chronic gingivitis. Ain Shams Dental Journal, 211-219. (Year: 2007).

Verguard et al., "Mineral-binding milk proteins and peptides; occurrence, biochyemical and technological characteristics", British Journal of Nutrition, Nov. 2000; 84: Suppl. 1, S91-S98.

White, A return to stannous fluoride dentrifices, Journal of clinical dentistry, Feb. 1995; Spec No. 29-36.

"GC stellt Kasein-haltige Zahnschutzcreme vor—Vorbeugen statt reparieren", DZW Special IDS-Nachlese, 2005, English Abstract, 7 pages.

"MI Paste and MI Paste Plus", [retrieved on Oct. 21, 2014] from http://web.archive.org/web/20131223044114/http://www.gcamerica.com/products/preventive/MI_Paste, published on Dec. 23, 2013 as per Wayback Machine, 2 pages.

"Minimale Intervention fur Maximale Mundgesundheit", DZW Special, 2005, English Abstract, 1 page.

"Minimum Intervention: modernes Kariesmanagement—Weg vom chirurgischen, hin zum medizinischen Versorgungsansatz mit GC", IDS—31st International Dental Show, Cologne, Apr. 12-16, 2005 (Today—Independent Trade Show Daily- Saturday) English Abstract, 2 pages.

"Preventive Agents", The Dental Advisor, vol. No. 21, Issue No. 10, Dec. 2004, pp. 1-6.

(56) References Cited

OTHER PUBLICATIONS

"Products for the Dental Hygienist—Desensitizers", The Dental Advisor, vol. No. 23, Issue No. 6, Jul./Aug. 2006, 2 pages.

"Tooth Mousse—Pierre qui roule n'amasse pas mousse? Ben si!", Clinic, vol. No. 27, Apr. 2006, pp. 218-219.

"Caseine phosphopeptide et phosphate de calcium amorphe: un complexe prometteur", Dialogue Dentaire, Printemps, 2005/W30, pp. 27-29, English Abstract provided.

"Editors' Choice Products—Prospec MI Paste", The Dental Advisor, vol. No. 22, Issue No. 5, Jun. 2005, 1 page.

"GC Tooth Mousse—Eine ganz andere Art der Prävention," Dental Spiegel, Feb. 2005, pp. 53-54.

"Putting mouths where the money is", DPRAsia, Jan./Feb. 2007, pp. 8-10.

"Tradition und modernes know how—ein Erfolgsrezept", Zahn Prax, vol. No. 8, Issue No. 5, 2005, p. 267.

Adamson, N. et al., "The analysis of multiple phosphoseryl-containing casein peptides using capillary zone electrophoresis", J. of Chromatography, vol. No. 646, Jun. 1993, pp. 391-396.

Adamson, N.J. et al., "Characterization of casein phosphopeptides prepared using alcalase: Determination of enzyme specificity", Enzyme and Microbial Tech., vol. No. 19, Aug. 1996, pp. 202-207.

Adamson, N.J. et al., "Characterization of Tryptic Casein Phosphopeptides Prepared Under Industrially Relevant Conditions", Biotec. and Bioeng., vol. No. 45, Issue No. 3, Feb. 1995, pp. 196-204.

Adamson, N.J. et al., "High performance capillary electrophoresis of casein phosphopeptides containing 2-5 phosphoseryl residues: Relationship between absolute electrophoretic mobility and peptide charge and size", Electrophoresis, vol. No. 16, 1995, pp. 525-528.

Adebayo, O.A. et al., "Effects of conditioners on microshear bond strength to enamel after carbamide peroxide bleaching and/or casein phosphopeptide-amorphous calcium phosphate (CPP-ACP) treatment", Journal of Dentistry, vol. No. 35, 2007, pp. 862-870.

Akinmade, A.O. et al., "Review Glass-Ionomer Cements as Adhesives, Part I, Fundamental Aspects and Their Clinical Relevance," Journal of Materials Science: Materials in Medicine, vol. No. 4, 1993, pp. 95-101.

Al-Zraikat, H. et al., "Development of glass ionomer cement incorporating casein phosphopeptide amorphous calcium phosphate (CPP-ACP) complex", Australian Dental Journal ADRF Special Research Supplement, vol. No. 52, Issue No. 4, 2007, p. S4.

Al-Zraikat, H. et al., "Incorporation of Casein-Phosphopeptide-Amorphous Calcium Phosphate into Glass Ionomer Cement", Abstract 0654, 84th General Session of the IADR, Jun. 28-Jul. 1, 2006, Brisbane, Australia, 1 page.

Allais, G., "Karies—Die Therapie", Journal of Continuing Dental Education, Jun. 2007, pp. 716-735.

Angmar, B. et al., "Studies on the Ultrastructure of Dental Enamel—IV. The Mineralization of Normal Human Enamel", J. Ultrastructure Research, vol. No. 8, 1963, pp. 12-23.

Aoba, T. et al., "Dental Fluorosis: Chemistry and Biology", Crit. Rev Oral Biol. Med., vol. No. 13, Issue No. 2, 2002, pp. 155-170.

Ardu, S. et al., "A minimally invasive treatment of severe dental fluorosis", Quintessence International, vol. No. 38, Issue No. 6, Jun. 2007, pp. 455-458.

Ardu, S. et al., "Minimally invasive treatment of white spot enamel lesions", Quintessence International, vol. No. 38, Issue No. 8, Sep. 2007, pp. 633-636.

Aytepe, Z. et al., "Effect of CCP-ACP on Oral Health of Cerebral Palsy Children", Abstract 3343, Jul. 2008, International Association for Dental Research, Toronto, Canada, 1 page.

Baig, A. et al., "HAP Dissolution Study II: SnF2 vs. NaF Dentifrice Study". 87th Session of the IADR (International & American Associations for Dental Research) Apr. 1-4, 2009 [online], [retrieved on Oct. 21, 2014]. Retrieved from internet, URL: dentalcare.com/media/en-us/research_ db/pdf/, p. 24.

Basting, RT et al., "The Effect of 10% Carbamide Peroxide Bleaching Material on Microhardness of Sound and Demineralized Enamel and Dentin In Situ" {Clinical Research} Operative Dentistry, vol. No. 26, 2001, pp. 531-539.

Bavetta, L.A. et al., "Protein Factors and Experimental Rat Caries", The Journal of Nutrition, vol. No. 63, 1957, pp. 107-117.

Benzian, H. et al., "Total and free available fluoride in toothpastes in Brunei, Cambodia, Laos, the Netherlands and Suriname", International Dental Journal, vol. No. 62, 2012, pp. 213-221.

Biesbrock, A.R. et al., "Reversal of Incipient and Radiographic Caries Through The Use of Sodium and Stannous Fluoride Dentifrices in a Clinical Trial," The Journal of Clinical Dentistry vol. No. IX, Issue No. 1, Feb. 1998, pp. 5-10.

Biesbrock, Aaron R. et al., "Dose response efficacy of sodium fluoride dentifrice at 9 and 21 months with supervised brushing", American Journal of Dentistry, vol. No. 16, Issue No. 5, Oct. 2003, 305-312.

Biesbrock, Aaron R., "Relative anti-caries efficacy of 1100, 1700, 2200, and 2800 ppm fluoride ion in a sodium fluoride dentifrice over 1 year", Community Dentistry and Oral Epidemiology, vol. No. 29, Jan. 2001, pp. 382-389.

Black, G.V. et al., "Mottled Teeth: An Endemic Developmental Imperfection of the Enamel of the Teeth Heretofore Unknown in the Literature of Dentistry", The Dental Cosmos, vol. No. LVIII, Issue No. 2., Feb. 1916, pp. 129-156.

Burwell, A.K. et al. "Dentifrice Protection Against Dentin Demineralization in an In Vitro Study", Abstract 1764, IADR, New Orleans, USA, Mar. 2007, 2 pages.

Burwell, A.K. et al., "Quantitative Tubule Occlusion in an In Vitro Remineralization/Demineralization Model", Abstract 0568, EADR 2006, Dublin, Ireland, Sep. 2006, 3 pages.

Cai, F. et al., "Effect of Addition of Citric Acid and Casein Phosphopeptide-Amorphous Calcium Phosphate to a Sugar-Free Chewing Gum on Enamel Remineralization in Situ", Caries Research, vol. No. 41, Feb. 2007, pp. 377-383.

Cai, F. et al., "Remineralization by Chewing Gum Containing CPP-ACP and Citric Acid", Abstract 190, 84th General Session of the IADR, Brisbane, Australia, Jun. 28, 2006-Jul. 1, 2006, pp. 240-243.

Cai, F. et al., "Remineralization of enamel subsurface lesions in situ by sugar-free lozenges containing casein phosphopeptide-amorphous calcium phosphate", Aus. Dent. J., vol. No. 48, Issue No. 4, 2003, pp. 240-243.

Calcium Glycerophosphate, DrugBank, pp. 1-5, XP002783472 (created Mar. 12, 2015) (retrieved Jul. 31, 2018).

CAPLUS, "NMR studies of a novel Calcium, phosphate and fluoride delivery vehicle <SYM97> S1-casein(59-79) by stabilized amorphous calcium fluoride phosphate nanocomplexes", Copyright 2005, 4 pages.

Carrillo, J. et al., "Nuevos avances tecnológicos en Odontologia Conservadora", La Gaceta Dental, vol. No. 193, Issue No. 213, Jun. 2008, pp. 218-219.

Chalmers, J. et al., "Minimal Intervention Dentistry in the New Millennium", Dentaltown, Feb. 2008, 2 pages.

Chalmers, J.M., "Minimal intervention dentistry: part 1. Strategies for Addressing the New Caries Challenge in Older Patients", JCDA, vol. No. 72, Issue No. 5, Jun. 2006, pp. 427-433.

Chapple, I.L.C. et al., "Primary prevention of periodontitis: managing gingivitis", Journal of Clinical Periodontology, vol. No. 42, Suppl. 16, 2015, pp. S71-S76.

Chelariu, C. et al., "Nuove prospettive nella prevenzione della carie Congresso Nazionale del Collegio dei Docenti di Odontoiatria Roma", Apr. 5-7, 2006, Poster session, published by "Doctor Os", No. 3, Mar. 2006, English Abstract, 1 page.

Chen, L. et al., "Calcium Release and Mechanical Properties of Experimental Calcium-Releasing Composites", Abstract 2572, IADR, New Orleans, USA, Mar. 2007, 1 page.

Chen, Y. et al., "Research progress of complex of casein phosphopeptide and amorphous calcium phosphate in oral therapy", Chin. J. Aesth. Med., vol. No. 23, Issue No. 8, 2014, pp. 681-683.

CIE Technical Committee, "Colorimetry—Second Edition", Publication CIE No. 15.2, 1986, 85 pages.

(56)            References Cited

OTHER PUBLICATIONS

Cipolla, M. et al., "Fluoride and Calcium-Phosphate Effects on Fracture Toughness of Bleached Dentin", Abstract 1032, Toronto, Canada, Jul. 2008, 4 pages.

Coates, L., "Tooth mousse shows some unexpected beneficial side effects", Dental Asia, Nov./Dec. 2004, pp. 40-43.

Cochrane, N.J. et al., "QLF and TMR analysis of CPP-ACFP remineralized enamel in vitro", Abstract 192—84th General Session of the IADR, Brisbane, Australia Jun. 28, 2006-Jul. 1, 2006, 1 page.

ColgatePalmolive, "Fluoride Conversions" dated Feb. 2013. www.colgateprofessional.com (2013).

Comar, L.P. et al., "Effect of NaF, SnF2, andTiF4 Toothpastes on Bovine Enamel and Dentin Erosion-Abrasion In Vitro", International Journal of Dentistry, vol. No. 2012, Article ID 134350, pp. 1-6.

CPP-ACP_and_gingivitis_Google_Scholar_12-13-21.pdf, 2021, 2 pages.

Crisp, S. et al., "Glass Ionomer Cements: Chemistry of Erosion", J. Dent. Res., vol. No. 55, Issue No. 6, 1976, pp. 1032-1041.

Cross, K.J. et al., "Casein Phosphopeptide-Amorphous Calcium Phosphate Nanocomplexes: A Model of the Casini Micelle Core", Centre for Oral Health Science, School of Dental Science, The University of Melbourne, 2008, pp. 1-42.

Cross, K.J. et al., "Casein Phosphopeptides in Oral Health—Chemistry and Clinical Applications", Current Pharmaceutical Design, vol. No. 13, Issue No. 8, 2007, pp. 793-800.

Cross, K.J. et al., "Cation-dependent structural features of beta-casein-(1-25)", Biochem. J., vol. No. 356, 2001, pp. 277-286.

Cross, K.J. et al., "NMR studies of a novel calcium, phosphate and fluoride delivery vehicle-alphaS1-casein(59-79) stabilized amorphous calcium fluoride phosphate nanocomplexes", Biomaterials, vol. No. 25, 2004, pp. 5061-5069.

Cross, K.J. et al., "Physicochemical Characterization of Casein Phosphopeptide-Amorphous Calcium Phosphate Nanocomplexes", The Journal of Biological Chemistry, vol. No. 280, Issue No. 15, 2005, pp. 15362-15369.

Cross, K.J. et al., "Structural Studies of the b-Casein Phosphopeptide Bound to Amorphous Calcium Phosphate", J. Dent. Res., vol. No. 80, IADR Abstracts, Abstract 0490, 2001, p. 588.

Cross, K.J. et al., "Structure and 15N-Dynamics of Casein Phosphopeptide-Amorphous Calcium Phosphate Nanocomplexes", Abstract 2534, 84th General Session of the IADR, Jun. 28-Jul. 1, 2006, Brisbane, Australia, 1 page.

Cross, K.J. et al., "Ultrastructural Studies of the Casein Phosphopeptide-Amorphous Calcium Phosphate Nanoclusters", J. Dent. Res., vol. No. 80, IADR Abstracts, Abstract 0491, 2001, p. 588.

Cross, KJ et al., "Structural characterization of anticariogenic casein phosphopeptide alpha-s2 casein(46-70) complexed with amorphous calcium phosphate", Aust Dent J ADRF Special Research Supplement, vol. No. 52, Issue No. 4, 2007, pp. S10-S11.

Cross, KJ et al., "Structural Characterization of Beta-casein(1-25)-ACFP Complex", Aust Dent J ADRF Special Research Supplement, vol. No. 52, Issue No. 4, 2007, p. S12.

Curnow, M.M.T. et al., "A Randomised Controlled Trial of the Efficacy of Supervised Toothbrushing in High-Caries-Risk Children", Caries Research, vol. No. 36, 2002, pp. 294-300.

Database WPI Week 200316, Thomason Scientific, London, GB, 2003-165149, XP002537968 & SE 0 100 558 A, Mediteam Dental AB, Aug. 21, 2002, Abstract, 2 pages.

Davies, G.M. et al., "A randomized controlled trial of the effectiveness of providing free fluoride toothpaste from the age of 12 months on reducing caries in 5-6 year old children", Community Dental Health, vol. No. 19, 2002, pp. 131-136.

De Oliveira, A. et al., "In situ effect of a CPP-ACP chewing gum on enamel erosion associated or not with abrasion", Clin Oral Investig, vol. No. 21, Mar. 2016, pp. 339-346.

Deangelis, A.F. et al., "Molecular modelling of anticariogenic casein phosphopeptide aS2-CN(2-20) NMR spectroscopy derived constraints", Abstract 2997, 82nd General Session of the IADR, Mar. 2004, Honolulu, Hawaii, 1 page.

Denbesten, P.K. et al., "Biological Mechanisms of Fluorosis and Level and Timing of Systemic Exposure to Fluoride with Respect to Fluorosis", J Dent Res, vol. No. 71, Issue No. 5, May 1992, pp. 1238-1243.

Denes, G. et al., "Oxidation of SnF2 stannous fluoride in aqueous solutions", Hyperfine Interactions, vol. No. 90, 1994, pp. 435-439.

Donovan, T., "Protocol for the prevention and management of root caries", Journal Compilation, vol. No. 20, Issue No. 6, 2008, pp. 405-411.

Duckworth, R.M. et al., "Effects of Mouthwashes of Variable NaF Concentration but Constant NaF Content on Oral Fluoride Retention", Caries Research, vol. No. 28, 1994, pp. 43-47.

Duckworth, R.M. et al., "Oral Fluoride Measurements for Estimation of the Anti-caries Efficacy of Fluoride Treatments", J Dent Res, vol. No. 71, Spec Iss, Apr. 1992, pp. 836-840.

Fahad, A.H. et al., "Effect of casein phosphopeptide-amorphous calcium phosphate on the microhardness and microscopic features of the sound enamel and initial caries-like lesion of permanent teeth, compared to fluoridated agents," Journal of Baghdad College Dentistry, vol. No. 24, Issue No. 4, 2012, pp. 114-120.

Farooq, I. et al., "A review of novel dental caries preventative material: Casein phosphopeptide-amorphous calcium phosphate (CPP-ACP) complex," King Saud University Journal of Dental Sciences, vol. No. 4, 2013, pp. 47-51.

Featherstone, J.D.B. et al., "An in situ Model for Simultaneous Assessment of Inhibition of Demineralization and Enhancement of Remineralization", J Dent Res, vol. No. 71, Spec. Iss., Apr. 1992, pp. 804-810.

Feinmann, J., "This won't hurt a bit," The Times, body&soul news, Mar. 12, 2005, pp. 4-5.

Fejerskov, O. et al., "The Effect of Fluoride on Tooth Mineralization", Fluoride in Dentistry—2nd edition, Chapter 8, Munksgaard, Copenhagen, 1996, pp. 112-152.

Fejerskov, O. et al., "Dental fluorosis—a handbook for health workers", Munksgaard, Copenhagen, 1988, pp. 32-77.

Fejerskov, O. et al., "Posteruptive changes in human dental fluorosis—a histological and ultrastructural study", Proc Finn Dent Soc, vol. No. 87, Issue No. 4, 1991, pp. 607-619.

Fejerskov, O. et al., "The Nature and Mechanisms of Dental Fluorosis in Man", J Dent Res, vol. No. 69, Spec Iss, Feb. 1990, pp. 692-700.

Ferrazzano, G.F. et al., "New Strategies in dental caries prevention: experimental study on casein phosphopetides", European Journal of Paedetric Dentistry, vol. No. 4, 2007, pp. 183-187.

Ferrazzano, G.F. et al., "Protective effect of yogurt extract on dental enamel demineralization in vitro", Australian Dental Journal, vol. No. 53, 2008, pp. 314-319.

Freml, L. et al., "Efficacy of Hypersensitivity Agents on Demineralization under Provisional Crowns", Abstract 1346, IADR Mar. 2007, New Orleans, USA, 2 pages.

Fuller, B.L. et al., "Efficacy of MI Paste in Preventing Demineralization in Overdenture Abutments", Abstract 0503, IADR Mar. 2007, New Orleans, USA, 2 pages.

Gagnaire, V. et al., "Phosphopeptides interacting with colloidal calcium phosphate isolated by tryptic hydrolysis of bovine casein micelles", Journal of Dairy Research, vol. No. 63, 1996, pp. 405-422.

Gandolfi, M.G. et al., "Calcium silicate coating derived from Portland cement as treatment for hypersensitive dentine", Journal of Dentistry, vol. No. 36, 2008, pp. 565-578.

GC America, Inc. "MI Paste™ and MI Paste Plus™ with Recaldent™ (CPP-ACP)", Inside Dentistry, vol. No 8, Issue No. 10, Oct. 2012 [online], [retrieved on Oct. 21, 2014]. Retrieved from internet, URL: www .dentalaegis.com/id/201 21 1 O/mi-paste-and-mi-paste-p 1 us-with-recaldent-cpp-acp>, 6 pages.

Giambro, N.J. et al., "Characterization of Fluorosed Human Enamel by Color Reflectance, Ultrastructure, and Elemental Composition", Caries Res., vol. No. 29, 1995, pp. 251-257.

Giniger, M. et al., "A 180-Day Clinical Investigation of the Tooth Whitening Efficacy of a Bleaching Gel with Added Amorphous Calcium Phosphate", J. of Clinical Dentistry. vol. No. 16, Issue No. 1, 2005, pp. 11-16.

(56)        References Cited

OTHER PUBLICATIONS

Giniger, M. et al., "The clinical performance of professionally dispensed bleaching gel with added amorphous calcium phosphate", JADA, vol. No. 136, Mar. 2005, pp. 383-392.

Gisselsson, H., et al., "Effect of professional flossing with NaF or SnF2 gel on approximal caries in 13-16-year-old schoolchildren", Acta Odontologica Scandinavica, vol. No. 57, Issue No. 2, 1999, pp. 121-125.

Gugnani, S. et al., "Comparative evaluation of two commercially available desensitizing agents after scaling and root planing: an in vivo study", PERIO, vol. No. 5, Issue No. 2, 2008, pp. 121-129.

Haderlie, D.C. et al., "MI Paste and Fluoride effects on Secondary Caries", Abstract 0504, IADR Mar. 2007, New Orleans, USA, 2 pages.

Harper, D.S. et al., "Cariostatic Evaluation of Cheeses with Diverse Physical and Compositional Characteristics", Caries Res., vol. No. 20, 1986, pp. 123-130.

Harper, D.S. et al., "Modification of Food Cariogenicity in Rats by Mineral-Rich Concentrates from Milk", J. Dent Res., vol. No. 66, Issue No. 1, Jan. 1987, pp. 42-45.

Hartshorne, JE et al., "The relationship between plaque index scores, fluoride content of plaque, plaque pH, dental caries experience and fluoride concentration in drinking water in a group of primary school children", Journal of the Dental Association of South Africa, Vo. No. 49, Jan. 1994, pp. 5-10.

Hay, K.D. et al., "A Clinical Trial of the Anticaries Efficacy of Casein Derivatives Complexed with Calcium Phosphate in Patients with Salivary Gland Dysfunction", Oral. Surg. Oral Med Oral. Pathol Oral Radiol. Endod., vol. No. 93, Issue No. 3, Mar. 2002, pp. 271-275.

Haywood, V.B. et al., "History, safety, and effectiveness of current bleaching techniques and applications of the nightguard vital bleaching technique", Quintessence Int., vol. No. 23, Issue No. 7, Jul. 1992, pp. 471-488.

Hicks, J. et al., "Biological factors in dental caries: role of remineralization and fluoride in the dynamic process of demineralization and remineralization (part 3)", The Journal of Clinical Pediatric Dentistry, vol. No. 28, Issue No. 3, 2004, pp. 203-214.

Hicks, J. et al., "Casein Phosphopeptide-Amorphous Calcium Phosphate Paste: Root Surface Caries Formation", Abstract 3275, IADR, Baltimore, Maryland, Mar. 2005, 1 page.

Hidaka, S. et al., "A New Method for Study of the Formation and Transformation of Calcium Phosphate Precipitates: Effects of Several Chemical Agents and Chinese Folk Medicines", Archives of Oral Biol., vol. No. 36, Issue No. 1, 1991, pp. 49-54.

Holler, B.E. et al., "Fluoride uptake and distribution in enamel and dentin after application of different fluoride solutions", Clin Oral Invest, vol. No. 6, 2002, pp. 137-144.

Holloway, P.J. et al., "Effects of Various Sucrose: Casein Ratios in Purified Diets on the Teeth and Supporting Structures of Rats", Arch. Oral Biol., vol. No. 3, 1961, pp. 185-200.

Holt, C. et al., "Ability of a b-casein phosphopeptide to modulate the precipitation of calcium phosphate by forming amorphous dicalcium phosphate nanoclusters", Biochem J., vol. No. 314, 1996, pp. 1035-1039.

Holt, C., "An equilibrium thermodynamic model of the sequestration of calcium phosphate by casein micelles and its application to the calculation of the partition of salts in milk", European Biophysics Journal, 2004, pp. 421-434.

Huang, A. et al., "Remineralization of Eroded Teeth Using CPP-ACP Paste", Abstract 3267, International Association for Dental Research, Toronto, Canada, Jul. 2008, 1 page.

Huq, N.L. et al., "Nascent Helix in the Multiphosphorylated Peptide as2-Casein(2-20)", Journal of Peptide Science, vol. No. 9, 2003, pp. 386-392.

Huq, N.L. et al., "A 1H-NMR study of the casein phosphopeptide as1-casein (59-79)", Biochimica et Biophysica Acta, vol. No. 1247, 1995, pp. 201-208.

Huq, N.L. et al., "Molecular Modeling of a Multiphosphorylated Sequence Motif Bound to Hydroxyapatite Surfaces", J. Mol. Model., vol. No. 6, 2000, pp. 35-47.

Huq, N.L. et al., "Molecular modelling of the multiphosphorylated casein phosphopeptide aS1-casein(59-79) based on NMR constraints", J. Dairy Res., vol. No. 71, 2004, pp. 28-32.

Iijima, Y. et al., "Acid Resistance of Enamel Subsurface Lesions Remineralized by a Sugar-Free Chewing Gum Containing Casein Phosphopeptide-Amorphous Calcium Phosphate", Caries Res., vol. No. 38, 2004, pp. 551-556.

Iijima, Y. et al., "Acid Resistance of Remineralized Enamel by a Sugar-Free Chewing Gum", Abstract 0184, 84th General Session of the IADR, Jun. 28-Jul. 1, 2006, Brisbane, Australia, 1 page.

Imfeld, T., "Prevention of progression of dental erosion by professional and individual prophylactic measures," Eur J Oral Sci, vol. No. 104, 1996, pp. 215-220.

Inaba, D. et al. "Intraoral changes in NaOCl-treated Root Dentin Lesions: A Pilot Study.", J. Dental Health, vol. No. 50, 2000, pp. 824-826, Abstract.

Inaba, D. et al., "Effect of Sodium Hypochlorite Treatment on Remineralization of Human Root Dentine in vitro", Caries Research, vol. No. 30, 1996, pp. 218-224.

International Preliminary Report on Patentability on PCT Appl. Ser. No. PCT/AU2020/050236 dated Aug. 25, 2021 (11 pages).

International Search Report and Written Opinion on PCT Appl. Ser. No. PCT/AU2020/050236 dated May 22, 2020 (18 pages).

Kandelman, D et al., "A 24-month Clinical Study of the Incidence and Progression of Dental Caries in Relation to Consumption of Chewing Gum Containing Xylitol in School Preventive Programs", J Dent Res, vol. No. 69, Issue No. 11, Nov. 1990, pp. 1771-1775.

Kariya, S. et al., "Fluoride Effect on Acid Resistance Capacity of CPP-ACP Containing Material", Abstract 2045, 82nd General Session of the IADR, Mar. 2004, Honolulu, Hawaii, 1 page.

Kariya, S. et al., "Remineralization of Enamel Lesion by a Novel Cream with both CPP-ACP and Fluoride", Poster Session 136, 54th Annual ORCA Congress, 2007, 1 page.

Keçik, D. et al., "Effect of Acidulated Phosphate Fluoride and Casein Phosphopeptide-Amorphous Calcium Phosphate Application on Shear Bond Strength of Orthodontic Brackets", Angle Orthodontist, vol. No. 78, Issue No. 1, 2008, pp. 129-133.

Khan, S., "White Spots on Teeth", Buzzle.com, https://www.buzzle.com/articles/white-spots-on-teeth.html, published Jan. 8, 2010, 2 pages.

Kilian, M. et al., "The oral microbiome—an update for oral health-care professionals", British Dental Journal, vol. No. 221, Issue No. 10, Nov. 18, 2016, pp. 657-666.

Kim, K.-B. et al., "Remineralization of the artificial caries lesion using CPP-ACP and fluoride", Abstract 3280, International Association for Dental Research, Toronto, Canada, Jul. 2008, 1 page.

Kowalczyk, A. et al., "Evaluation of the product based on Recaldent™ technology in the treatment of dentin hypersensitivity", Advances in Medical Sciences, vol. No. 51, Suppl. 1, 2006, pp. 40-42.

Krobicka, A. et al., "The Effects of Cheese Snacks on Caries in Desalivated Rats", J. Dent Res., vol. No. 66, Issue No. 6, Jun. 1987, pp. 1116-1119.

Kumar, VLN et al., "The effect of casein phosphopeptide-amorphous calcium phosphate on remineralization of artificial caries-like lesions: an in vitro study", Australian Dental Journal, vol. No. 53, 2008, pp. 34-40.

Lasfargues, J. et al., "La Remineralisation Des Lesions Carieuses (2) Synergies Therapautiques", Realites Cliniques, vol. No. 15, Issue No. 3, 2004, pp. 261-275, English Abstract.

Legeros, R.Z., "Calcium Phosphates in Demineralization/Remineralization Processes", J Clinical Dent, vol. No. 10, Issue No. 2, 1999, pp. 65-73.

Lewis, J., "Brush, floss and mousse?", Women Dentistry Journal, Winter 2005, vol. No. 2, Issue No. 4, pp. 18-19.

Little, E. et al., "An equilibrium thermodynamic model of the sequestration of calcium phosphate by casein phosphopeptides", European Biophysics Journal, vol. No. 33, 2004, pp. 435-447.

(56) References Cited

OTHER PUBLICATIONS

Llena, C. et al., "Anticariogenicity of Casein Phosphopeptide-amorphous Calcium Phosphate: A Review of the Literature", The Journal of Contemporary Dental Practice, vol. No. 10, Issue No. 3, May 2009, pp. 1-9.

Loesche, W.J., "Role of *Streptococcus mutans* in Human Dental Decay", Microbial. Rev., vol. No. 50, Issue No. 4, Dec. 1986, pp. 353-380.

Lynch, R.J.M. et al, "Low-Levels of fluoride in plaque and saliva and their effects on the demineralisation and remineralisation of enamel; role of fluoride toothpastes", International Dental Journal, vol. No. 54, Issue No. 5, pp. 304-309.

Malcmacher, L., "Enamel Remineralization: The Medical Model of Practicing Dentistry", Dentistry Today, Nov. 2006, 2 pages.

Malcmacher, L., "Vitamins for teeth", Common Sense Dentistry, www.dentaleconomics.com, Oct. 2006, pp. 130 and 144.

Manton, D.J. "Dental Caries: Where to From Here?", Ann Roy Australas Coll Dent Surg, vol. No. 19, 2008, pp. 73-76.

Manton, D.J. et al., "In Situ Remineralisation by Sugar-Free Gums, One Containing CPP-ACP", Abstract 0020, 45th Annual Meeting of Australian/New Zealand Division of the IADR, Sep. 2005, 1 page.

Manton, D.J. et al., "Remineralization of enamel subsurface lesions in situ by the use of three commercially available sugar-free gums", International Journal of Paediatric Dentistry, vol. No. 18, 2008, pp. 284-290.

Manton, D.J. et al., "Remineralization of White Spot Lesions in situ by Tooth Mousse", Abstract 0185, 84th General Session of the IADR, Jun. 28-Jul. 1, 2006, Brisbane, Australia, 1 page.

Manton, D.J., "Promoting Remineralization: Using Casein Phosphopeptide-Stabilized Amorphous Calcium (Fluoride) Phosphate. A Chemical Approach", EAPD, Amsterdam, Jun. 8-11, 2006, 1 page.

Manton, DJ et al., "Effect of ozone and Tooth Mousse™ on the efficacy of peroxide bleaching", Australian Dental Journal, vol. No. 53, 2008, pp. 128-132.

Martinez-Pablon, M. et al., "Comparison of the Effect of Two Sugar-Substituted Chewing Gums on Different Caries- and Gingivitis-Related Variables: A Double-Blind, Randomized, Controlled Clinical Trial", Clinical Oral Investigations, vol. No. 18, 2014, pp. 589-598.

Mazzaoui, S.A. et al., "Incorporation of Casein Phosphopeptide-Amorphous Calcium Phosphate into a Glass-ionomer Cement", Journal of Dental Research, vol. No. 82, Issue No. 11, 2003, pp. 914-918.

Melkers, M.J., "Keeping Focused on the Finish Line . . . Accomplishing Goals with Traditional and Progressive Technologies", Dentaltown, vol. No. 5, Issue No. 11, Nov. 2004, pp. 60, 62, 64 & 66.

Mellberg, J.R. et al., "Effect of soluble calcium on fluoride uptake by enamel from sodium monofluorophosphate", J Dent Res., vol. No. 61, Issue No. 12, Dec. 1982, pp. 1394-1396.

MI Paste™ and MI Paste Plus™ [retrieved on Feb. 16, 2015] Retrieved from internet , URL: http://web.archive.org/web/20140701070616/http://www.mipaste.com/about.php> published on Dec. 4, 2013 as per Wayback Machine whole document Wayback machine used to determine publication date, 2 pages.

Mickenautsch, S., "An Introduction to Minimal Intervention Dentistry (MI)", Dental News, vol. No. XIV, Issue No. IV, 2007, pp. 13-20.

Milnar, F.J., "Considering Biomodification and Remineralization Techniques as Adjuncts to Vital Tooth-Bleaching Regimens", Compendium, vol. No. 28, Issue No. 5, May 2007, pp. 234-240.

Min, S. et al., "Progress in the treatment of dentin hypersensitivity", Anhui Medical and Pharmaceutical Journal, vol. No. 16, Issue No. 10, Oct. 2012, pp. 1521-1523 (Original and English translation attached).

Minami, K. et al., "Effects of Cheese and Milk Containing CPP-ACP on Enamel Remineralization", 2049—82nd General Session of the IADR, Mar. 2004, Honolulu, Hawaii, 1 page.

Mintel, "Mineralising Toothpaste," from Database GNPD, Database Accession No. 1368327, Aug. 2010, 3 pages.

Misra, S. et al., "Early Childhood Caries—A Review", Dental Update, vol. No. 34, Dec. 2007, pp. 556-564.

Mitthra, S. et al., "Mineral Loss before and after Bleaching and Mineral Uptake on Application of Remineralizing Agent", Indian Journal of Multidisciplinary Dentistry and Endodontics, vol. No 1, Issue No. 1, Jan. 2010, 4 pages.

Miyazaki, M. et al., "Using Ultrasound Transmission Velocity to Analyze Demineralization of Tooth Substrate", Abstract 94, 52nd ORCA Congress, Jul. 2005, Indianapolis, USA, Caries Res, vol. No. 39, p. 319.

Morgan, M.V. et al. "A Clinical Trial Measuring White Spot Lesion Progression and Regression", Abstract 0112, Jul. 2008, Toronto, Canada, 1 page.

Morgan, M.V. et al., "CPP-ACP gum slows progression and enhances regression of dental caries", Abstract 2445, 84th General Session of the IADR, Jun. 28-Jul. 1, 2006, Brisbane, Australia, 1 page.

Morgan, M.V. et al., "The Anticariogenic Effect of Sugar-Free Gum Containing CPP-ACP Nanocomplexes on Approximal Caries Determined Using Digital Bitewing Radiography", Caries Research, vol. No. 42, 2008, pp. 171-184.

Morgan, MV et al., "Clinical Trial of Tooth Mousse on White Spot Lesions", Cooperative Research Centre for Oral Health Science, Briefing Paper No. 2, Jul. 2008, 4 pages.

Moule, C.A. et al., "Resin bonding using an all-etch or self-etch adhesive to enamel after carbamide peroxide and/or CPP-ACP treatment", Australian Dental Journal, vol. No. 52, Issue No. 2, 2007, pp. 133-137.

Mount, GJ, "A new paradigm for operative dentistry", Australian Dental Journal, vol. No. 52, Issue No. 4, 2007, pp. 264-270.

Munjal, D. et al., "Assessment of White Spot Lesions and In-Vivo Evaluation of the Effect of CPP-ACP on White Spot Lesions in Permanent Molars of Children", Journal of Clinical and Diagnostic Research, vol. No. 10, Issue No. 5, May 2016, pp. 149-154.

Murata, Y. et al., "Remineralization Power by Xylitol Chewing Gums", Abstract 2046, 82nd General Session of the IADR, 2004, Honolulu, Hawaii, 1 page.

Narayana, T. et al., "An in vitro study of wear prevention in dentine", Abstract 2424, 84th General Session of the IADR, Jun. 28-Jul. 1, 2006, Brisbane, Australia, 1 page.

Ng, F. et al., "Aesthetic management of severely fluorosed incisors in an adolescent female", Australian Dental Journal, vol. No. 52, Issue No. 3, 2007, pp. 243-248.

O'Hehir, T., "Caries—More Than a Filling", Hygientown.com, Jul./Aug. 2008, pp. 8-12.

Ono, T. et al., "Complexes of Casein Phosphopeptide and Calcium Phosphate Prepared from Casein Micelles by Tryptic Digestion", Biosci. Biotech. Biochem., vol. No. 58, Issue No. 8, 1994, pp. 1376-1380.

Ono, T. et al., "Preparation of Casein Phosphopeptides from Casein Micelles by Ultrafiltration", Biosci. Biotech. Biochem., vol. No. 59, Issue No. 3, 1995, pp. 510-511.

Oshiro, M. et al., "Effect of CPP-ACP paste on tooth mineralization: an FE-SEM study", Journal of Oral Science, vol. No. 49, Issue No. 2, 2007, pp. 115-120.

Pelletier, P. et al., "Study of the Hyrolyisis Reaction of the P03F2 Anion in Aqueous Solution", Z. Anorg. Alig. Chem., 1990, vol. No. 581, pp. 190-198.

Perdigao, J. et al., "Contemporary Trends and Techniques in Tooth Whitening: A Review", Practical Procedures & Aesthetic Dentistry, vol. No. 16, Issue No. 3, 2004, pp. 185-192.

Perich, J.W. et al., "Efficient Solution-Phase Synthesis of Multiple O-Phosphoseryl-Containing Peptides Related to Casein and Statherin", Int. J. Pept. Protein Res., vol. No. 40, 1992, pp. 81-88.

Perich, J.W. et al., "The Use of Synthetic Phosphopeptides for Epitope Mapping of the aS1-Casein Phosphopeptide Segment 59-70", Bioorg. Med. Chem. Lett., vol. No. 2, 1992, pp. 1153-1154.

Peschke, J.C. et al., "Nucleating Ability of Calcium Phosphate-Protein-Composites", Abstract 2244, IADR, Mar. 2007, New Orleans, USA, 2 pages.

(56) References Cited

OTHER PUBLICATIONS

Piekarz, C. et al., "An in vitro assessment of the role of Tooth Mousse in preventing wine erosion", Australian Dental Journal, vol. No. 53, 2008, pp. 22-25.

Pietrzycka, K. et al., "Chemical methods of treatment of dental caries: the action and application of CPP-ACP", Kwartalnik Stomatologa Praktyka Polish & English Journal for Dentists, E-Dentico, vol. No. 2, Issue No. 18, 2008, pp. 68-74.

Pitts, N.B., "Are We Ready to Move from Operative to Non-Operative/Preventive Treatment of Dental Caries in Clinical Practice?", Caries Res, vol. No. 38, 2004, pp. 294-304.

Plate, U. et al., "Investigation of the early mineralisation on collagen in dentine of rat incisors by quantitative electron spectroscopic diffraction (ESD)", Cell Tissue Res, vol. No. 278, 1994, pp. 543-547.

Poitevin, A. et al., "Clinical Effectiveness of a CPP-ACP Crème for Tooth Hypersensitivity Treatment", EADR Istanbul, Aug. 24-28, 2004, Abstract 0136, 1 page.

Quartarone, E. et al., "Surface kinetic roughening caused by dental erosion: an atomic force microscopy study", Journal of Applied Physics, vol. No. 103, 2008, 104702, 6 pages.

Rahiotis, C. et al., "Characterization of oral films formed in the presence of a CPP-ACP agent: An in situ study", Journal of Dentistry, vol. No. 36, 2008, pp. 272-280.

Rahiotis, C. et al., "Effect of a CPP-ACP agent on the demineralization and remineralization of dentine in vitro", Journal of Dentistry, vol. No. 35, 2007, pp. 695-698.

Ramadas, Y., "The oral care for children with malignancies", Synopses: The Newsletter of the Australian and New Zealand Society of Paediatric Dentistry, Issue No. 28, Mar. 2004, pp. 1-20.

Ramalingam, L. et al., "Adding Caesin Phosphopetide-amorphous Calcium Phosphate to Sports Drinks to Eliminate In Vitro Erosion", Pediatric Dentistry, vol. No. 27, Issue No. 1, 2005, pp. 61-67.

Ramalingam, L. et al., "An in Vitro Investigation of the Effects of Casein Phosphopeptide-Stabilized Amorphous Calcium Phosphate (CPP-ACP) on Erosion of Human Dental Enamel by a Sports Drink", J Dent Res., vol. No. 81, Spec Iss A, 2002, Abstract 2810, p. A-351.

Ramalingam, L. et al., "Erosion of Human Dental Enamel by Sports Drinks", Synopses, vol. No. 27, 2003, pp. 16-19.

Ranjitkar, S. et al., "Enamel wear prevention under conditions simulating bruxism and acid regurgitation", Abstract 2428, 84th General Session of the IADR, Jun. 28-Jul. 1, 2006, Brisbane, Australia, 1 page.

Ranjitkar, S. et al., "The Role of Tooth Mousse in preventing enamel wear," Poster 0375, Session 39, 42nd Annual Meeting of IADR, Continental European and Israeli Divisions, Sep. 26-29, 2007, 1 page.

Ranjitkar, S. et al., "The Role of Tooth Mousse in Reducing Erosive Tooth Wear", Abstract 2500, International Association for Dental Research, Jul. 2008, Toronto, Canada, 1 page.

Rees, J. et al., "Pronamel and tooth mousse: An initial assessment of erosion prevention in vitro", Journal of Dentistry, vol. No. 35, 2007, pp. 355-357.

Reeves, R. et al., "Calcium Phosphate Sequestering Phosphopeptide from Casein", Science, vol. No. 128, 1958, p. 472.

Reich, E., "Das kleine gewisse Etwas zur Remineralisation", Zahnmedizin, vol. No. 95, Issue No. 21, 2005, pp. 2-9, English Abstract.

Reich, E., "Die Betreuung von Kariespatienten in der Praxis", Quintessenz, vol. No. 59, Issue No. 12, 2008, pp. 1301-1307, English Abstract.

Reich, E., "Flüssiger Zahnschmelz", Dental Magazine, 2005, English Abstract, 4 pages.

Reich, E., "GC Tooth Mousse—Ein neuer Ansatz zur Remineralisation", Kongress: Wissenschaft und Praxis der Sanften Zahnheilkunde, Lindau am Bodensee, Mar. 3-4, 2006, English Abstract, 4 pages.

Reich, E., Dental Products Report Europe, Jan. 1, 2006, 9 pages.

Reynolds, E., "The Role of Phosphopeptides in Caries Prevention", Dental Perspectives, Edition 3, Nov. 1999, pp. 6-7.

Reynolds, E.C. et al., "Confectionary Composition and Rat Caries", Caries Res., vol. No. 21, 1987, pp. 538-545.

Reynolds, E.C. et al., "Effect of Adsorbed Protein on Hydroxyapatite Zeta Potential and Streptococcus mutans Adherence", Infection and Immunity, vol. No. 39, Issue No. 3, Mar. 1983, pp. 1285-1290.

Reynolds, E.C. et al., "Effect of Casein and Whey-Protein Solutions on Caries Experience and Feeding Patterns of the Rat", Archs. oral. Biol., vol. No. 29, Issue No. 11, 1984, pp. 927-933.

Reynolds, E.C. et al., "Enamel Remineralization by Chewing Gum Containing Casein Phosphopeptide-Amorphous Calcium Phosphate", J Dent Res, vol. No. 80, IADR Abstracts, Abstract 0489, 2001, p. 588.

Reynolds, E.C. et al., "Phosphoprotein Inhibition of Hydroxyapatite Dissolution", Calcif. Tissue Int., vol. No. 34, 1982, pp. S52-S56.

Reynolds, E.C. et al., "Protein Dissimilation by Human Salivary-sediment Bacteria", J. Dent.Res., vol. No. 68, Issue No. 1, Feb. 1989, pp. 124-129.

Reynolds, E.C. et al., "Reduction of Chocolate's Cariogenicity by Supplementation with Sodium Caseinate", Caries Res., vol. No. 21, 1987, pp. 445-451.

Reynolds, E.C. et al., "Retention in Plaque and Remineralization of Enamel Lesions by Various Forms of Calcium in a Mouthrinse or Sugar-free Chewing Gum", J Dent Res, vol. No. 82, Issue No. 3, 2003, pp. 206-211.

Reynolds, E.C. et al., "A Review of the Effect of Milk on Dental Caries", Aust. J. Dairy Tech., vol. No. 34, Dec. 1979, pp. 175-179.

Reynolds, E.C. et al., "A Selective Precipitation Purification Procedure for Multiple Phosphoseryl-Containing Peptides and Methods for Their Identification", Anal. Biochem., vol. No. 217, Issue No. 2, 1994, pp. 277-284.

Reynolds, E.C. et al., "Additional Aids to the Reminersalisation of Tooth Structure," Preservation and Restoration of Tooth Structure, Chapter 8, 2005, pp. 111-118.

Reynolds, E.C. et al., "Advances in Enamel Remineralization: Casein Phosphopeptide-Amorphous Calcium Phosphate", J. Clin. Dent., vol. No. X, Issue No. 2, 1999, pp. 86-88.

Reynolds, E.C. et al., "Anticariogenicity of Calcium Phosphate Complexes of Tryptic Casein Phosphopeptides in the Rat", J Dent Res, vol. No. 74, Issue No. 6, 1995, pp. 1272-1279.

Reynolds, E.C. et al., "Cariogenicity of a Confection Supplemented with Sodium Caseinate at a Palatable Level", Caries. Res., vol. No. 23., 1989, pp. 368-370.

Reynolds, E.C. et al., "Effect of Milk on Caries Incidence and Bacterial Composition of Dental Plaque in the Rat", Archs oral Biol., vol. No. 26, Issue No. 5, 1981, pp. 445-451.

Reynolds, E.C. et al., "Fluoride and Casein Phosphopeptide-Amorphous Calcium Phosphate", J Dent Res, vol. No. 87, Issue No. 4, 2008, pp. 344-348.

Reynolds, E.C. et al., "Improved Plaque Uptake and Enamel Remineralization by Fluoride with CPP-ACP", Abstract 2538, 84th General Session of the IADR, Jun. 28-Jul. 1, 2006, Brisbane, Australia, 1 page.

Reynolds, E.C., "The Prevention of Sub-surface Demineralization of Bovine Enamel and Change in Plaque Composition by Casein in an Intra-oral model", J. Dental Res., vol. No. 66, Issue No. 6, 1987, pp. 1120-1127.

Reynolds, E.C., "Anticariogenic Casein Phosphopeptides", Prot. Peptide Lett., vol. No. 6, Issue No. 5, 1999, pp. 295-303.

Reynolds, E.C., "Anticariogenic complexes of amorphous calcium phosphate stabilized by casein phosphopeptides: A review", Journal of Special Care in Dentistry, vol. No. 18, Issue No. 1, Jan./Feb. 1998, pp. 8-16.

Reynolds, E.C., "Calcium phosphate-based remineralizatron systems: scientific evidence?", Australian Dental Journal, vol. No. 53, 2008, pp. 268-273.

Reynolds, E.C., "Caries Prevention and Oral Health", Health Aspects of Dairy Products/Caries Prevention and Oral Health, 2002, pp. 1306-1313.

Reynolds, E.C., "Dairy Components in Oral Health", Aust. J. Dairy Tech., vol. No. 58, Issue No. 2, Aug. 2003, pp. 79-81.

Reynolds, E.C., "Dairy Products and Dental Health," Proceedings of the Nutrition Society of Australia, 1995, pp. 95-102.

(56) References Cited

OTHER PUBLICATIONS

Reynolds, E.C., "Remineralization of Enamel Subsurface Lesions by Casein Phosphopeptide-stabilized Calcium Phosphate Solutions", J Dent Res., vol. No. 76, Issue No. 9, Sep. 1997, pp. 1587-1595.

Reynolds, EC., "Remineralization of early enamel caries by anticariogenic casein phosphopeptide-amorphous calcium phosphate nanocomplexes", Dental Practice, Nov./Dec. 2001, 3 pages.

Roberts, A.J., "Role of Models in Assessing New Agents for Caries Prevention-Non-Fluoride Systems", Adv. Dent. Res., vol. No. 9, Issue No. 3, Nov. 1995, pp. 304-311.

Roberts, MJ et al., "Remineralisation of fluorotic enamel lesions by casein phosphopeptide-amorphous calcium fluorophosphate (CPP-ACFP) solution", IADR, ANZ Division, Abstract 54, 2000, 2 pages.

Robinson, C. et al., "Effect of Surface Zone Deproteinisation on the Access of Mineral Ions into Subsurface Carious Lesions of Human Enamel", Caries Res, vol. No. 24, 1990, pp. 226-230.

Rose, R.K., "Binding Characteristics of *Streptococcus mutans* for Calcium and Casein Phosphopeptide", Caries. Res., vol. No. 34, 2000, pp. 427-431.

Rose, R.K., "Effects of an Anticariogenic Casein Phosphopeptide on Calcium Diffusion in Streptococcal Model Dental Plaques", Archives of Oral Biology, vol. No. 45, 2000, pp. 569-575.

Rosen, S. et al., "Effect of Cheese, With and Without Sucrose, On Dental Caries and Recovery of *Streptococcus mutans* in Rats", J. Dent. Res., vol. No. 63, Issue No. 6, Jun. 1984, pp. 894-896.

Rozwadowska, E., "Children and private dentistry", Private Dentistry, May 2006, pp. 109-113.

Sakaguchi, Y. et al. "Remineralization Potential of CPP-ACP and its Synergy with Fluoride", Abstract 0191, 84th General Session of the IADR, Jun. 28-Jul. 1, 2006, Brisbane, Australia, 3 pages.

Sakaguchi, Y. et al., "Preventing Acid Induced Enamel Demineralization Using CPP-ACP Containing Paste", Abstract 2055, IADR, Mar. 2005, Baltimore, Maryland, USA, 1 page.

Sakr, A.M. et al., "The Effect of Recaldent (CPP-ACP) on the most putative bacteria in caries and chronic gingivitis", Ain Shams Dental Journal, vol. No. X, Issue No. 2, Jun. 2007, pp. 211-219.

Sato, T. et al., "Caries Prevention Potential of a Tooth-coating Material Containing Casein Phosphopeptide-Amorphous Calcium Phosphate (CPP-ACP)," IADR, General Session, Goteborg, 2003, Abstract 1007, 3 pages.

Schüpbach, P. et al., "Incorporation of Caseinoglycomacropeptide and Caseinophosphopeptide into the Salivary Pellicle Inhibits Adherence of Mutans Streptococci", J. Dent. Res, vol. No. 75, Issue No. 10, Oct. 1996, pp. 1779-1788.

Schweigert, B.S. et al., "Dental Caries in the Cotton Rat—VI. The Effect of the Amount of Protein, Fat and Carbohydrate in the Diet on the Incidence and Extent of Carious Lesions", J. Nutr., vol. No. 31, 1946, pp. 439-447.

Shaw, J.H., "Effects of dietary composition on tooth decay in the albino rat", J. Nutr., vol. No. 41, 1950, pp. 13-23.

Sheharyar, S. et al., "Efficacy of MI Paste For Sensitivity Associated With Vital Bleaching", Abstract 2041, IADR, Mar. 2007, New Orleans, USA, 2 pages.

Shen, P. et al., "Enamel remineralization by a mouthrinse containing casein phosphopeptide-amorphous calcium phosphate and fluoride in an in situ model", Australian Dental Journal ADRF Special Research Supplement, vol. No. 49, Issue No. 4, 2004, p. S19.

Shen, P. et al., "Remineralization of Enamel Subsurface Lesions by Sugar-free Chewing Gum Containing Casein Phosphopeptide-Amorphous Calcium Phosphate", J Dent Res, vol. No. 80, Issue No. 12, 2001, pp. 2066-2070.

Shen, P. et at., "Remineralization by a Mouthrinse Containing CPP-ACP at pH 5.5", Abstract 0189, 84th General Session of the IADR, Jun. 28-Jul. 1, 2006, Brisbane, Australia, 1 page.

Silva, M. et al., "Fluoride content of infant formulae in Australia", Australian Dental Journal, vol. No. 41, Issue No. 1, 1996, pp. 37-42.

Silva, M.F. de A. et al., "Effects of Water-soluble Components of Cheese on Experimental Caries in Humans", J Dent Res, vol. No. 66, Issue No. 1, Jan. 1987, pp. 38-41.

Sim, C. et al., "Anti-caries effect of CPP-ACP in irradiated nasopharyngeal carcinoma patients", Clinical Oral Investigations, vol. No. 19, Issue No. 5, 2015, pp. 1005-1011.

Skold-Larsson, K. et al., "Fluoride concentration in plaque in adolescents after topical application of different fluoride varnishes", Clin Oral Invest., vol. No. 4, 2000, pp. 31-34.

Slomiany, B.L. et al., "Salivary Mucins in Oral Mucosal Defense", Gen. Pharmac., vol. No. 27, Issue No. 5, 1996, pp. 761-771.

Smith, S. et al., "Ultramorphological evaluation of dentin after treatment with different desensitizing agents", Abstract 0941, IADR, 2007, New Orleans, USA, 2 pages.

Smolenski, D. et al., "MI Paste and Fluoride for Caries Prevention In-Vitro", Abstract 0505, IADR, 2007, New Orleans, USA, 2 pages.

Steinberg, S., "A Modern Paradigm for Caries Management, Part 1: Diagnosis and Treatment", Dentistry Today, Feb. 2007, 11 pages.

Steinberg, S., "A Modern Paradigm for Caries Management, Part 2: A Practical Protocol", Dentistry Today, Jun. 2007, 6 pages.

Stößer, L., et al., "Kariesprotektive Eigenschaften des durch Caseinphosphopeptid stabilisierten amorphen Calciumphosphat-Nanokomplexes (CPP-ACP)", Deutsche Zahniirztliche Zeitschrift, vol. No. 62, Issue No. 9, 2008, pp. 579-588.

Sudjalim, T.R. et al., "Prevention of demineralization around orthodontic brackets in vitro", American Journal of Orthodontics and Dentofacial Orthopedics., 2007, vol. No. 131, Issue No. 6, pp. 705.e1-705.e9.

Sudjalim, T.R. et al., "Prevention of white spot lesions in orthodontic practice: a contemporary review", Australian Dental Journal, vol. No. 51, Issue No. 4, 2006, pp. 284-289.

Sukasaem, H. et al., "Effect of CPP-ACP on Hardness of Enamel Eroded by Cola-drink", Abstract 1673, 84th General Session of the IADR, Jun. 28-Jul. 1, 2006, Brisbane, Australia, 1 page.

Supplementary European Search Report issued on Dec. 13, 2016 in EP Appl. Ser. No. EP14830019 (2 pages).

Takamizawa, T. et al., "Determination of Demineralization of Tooth Substrate by Use of an Ultrasonic Device", Japan J Conserv Dent, Jun. 47, Spring Issue 24, Abstract B-4, 2004, 2 pages.

Talbo, G.H. et al., "MALDI-PSD-MS Analysis of the Phosphorylation Sites of Caseinomacropeptide", Peptides, vol. No. 22, 2001, pp. 1093-1098.

Tantbirojn, D. et al., "Changes in surface hardness of enamel by a cola drink and a CPP-ACP paste", Journal of Dentistry, vol. No. 36, 2008, pp. 74-79.

Tay, L.Y. et al. "Assessing the Effect of a Desensitizing Agent Used Before In-office Tooth Bleaching," The Journal of the American Dental Association, vol. No. 140, Issue No. 10, Oct. 2009, pp. 1245-1251.

Ten Cate, J.M., "Current concepts on the theories of the mechanism of action of fluoride", Acta Odontol Scand, vol. No. 57, 1999, pp. 325-329.

Theerapiboon, U. et al., "Remineralization of Artificial Caries by CPP-ACP Paste", Abstract 3274, Jul. 2008, International Association for Dental Research, Toronto, Canada, 1 page.

Trajtenberg, C.P. et al., "CPP-ACP Paste with Fluoride: In Vitro Root Surface Caries Formation", Abstract 0500, IADR, 2007 New Orleans, USA, 2 pages.

Turssi, C.P. et al., "Progression of erosion following use of calcium and phosphorus compounds", Abstract 2499, Jul. 2008, International Association for Dental Research, Toronto, Canada, 1 page.

Ung, M. et al. "Investigation of the binding of casein phosphopeptides to the major enamel pellicle proteins", Australian Dental Journal ADRF Special Research Supplement, vol. 49, Issue No. 4, 2004, pp. S19-S20.

Vlacic, J. et al., "Combined CPP-ACP and photoactivated disinfection (PAD) therapy in arresting root surface caries: a case report", British Dental Journal, vol. No. 203, Issue No. 8, Oct. 27, 2007, pp. 457-459.

Walker, G. et al., "Increased remineralization of tooth enamel by milk containing added casein phosphopeptide-amorphous calcium phosphate", Journal of Dairy Research, vol. No. 73, 2006, pp. 74-78.

Walker, G.D. et al., "Consumption of milk with added casein phosphopeptide-amorphous calcium phosphate remineralizes enamel

(56)                References Cited

OTHER PUBLICATIONS subsurface lesions in situ", Australian Dental Journal, vol. No. 54, Issue No. 3, Sep. 2009, pp. 245-249.

Walsh, L., "Clinical applications of Recaldent products: which ones to use where", Australasian Dental Practice, May/Jun. 2007, pp. 144-146.

Walsh, L., "Clinical Aspects of Salivary Biology for the Dental Clinician", International Dentistry SA, vol. No. 9, Issue No. 4, 2007, pp. 22-41.

Walsh, L., "Tooth Mousse Information", GC Tooth Mousse Portfolio, 2nd Edition, Mar. 2005, 17 pages.

Walsh, L., "Topical CPP-ACP cremes beyond caries prevention", International Dentistry South Africa, vol. No. 4, Issue No. 5, 2014, pp. 26-32.

Walsh, L.J. et al., "Effect of CPP-ACP versus Potassium Nitrate on Cervical Dentinal Hypersensitivity", Abstract 0947, 84th General Session of the IADR, Jun. 28-Jul. 1, 2006, Brisbane, Australia, 1 page.

Walsh, L.J., "Application of the System for Total Environmental Management (STEM) to dysmineralization, dental erosion and tooth wear", Australasian Dental Practice, Jan./Feb. 2008, pp. 52-58.

Walsh, L.J., "The effects of GC Tooth Mousse on cervical dentinal sensitivity: a controlled clinical trial", International Dentistry SA—Australasian Edition, vol. No. 5, Issue No. 1, 2010, 7 pages.

Weiss, V., "Kariesprophylaxe in der kinderzahnärztlichen Praxis", ZWP, Oct. 2005, pp. 76-79.

Westerman, G. et al., "Argon Laser and Remineralizing Paste Effect on Root Surface Caries", Abstract 0018, IADR, Mar. 2007, New Orleans, USA, 2 pages.

Westerman, G. et al., "Argon Laser and Remineralizing Paste with Fluoride Effects on Enamel Caries," AAPD, Washington, 2008, 1 page.

White, D.J., "Use of Synthetic Polymer Gels for Artificial Carious Lesion Preparation", Caries Research, vol. No. 21, Issue No. 3, 1987, pp. 228-242.

Wikiel, K. et al., "Hydroxyapatite Mineralization and Demineralization in the Presence of Synthetic Phosphorylated Pentapeptides", Archives of Oral Biology, vol. No. 39, Issue No. 8, 1994, pp. 715-721.

Willershausen, B. et al., "In-Vitro-Studie Zur Überprufung einer möglichen Remineralisation durch caesinphosphopetidhaltige, amorphe Calciumphosphat-komplexe (CPP ACP)", Deutsche Zahnärztliche Zeitschrift, vol. No. 63, Issue No. 2, 2008, pp. 134-139.

William, V. et al., "Molar Incisor Hypomineralization: Review and Recommendations for Clinical Management", Pediatric Dentistry, vol. No. 28, Issue No. 3, 2006, pp. 224-232.

Wong, L. et al., "Plaque microcosm biofilm mineralisation by CPP-ACP and calcium-phosphate-monofluorophosphate-urea mineralising solution", Abstract 1269, 84th General Session of the IADR, Jun. 28-Jul. 1, 2006, Brisbane, Australia, 1 page.

Wong, R. et al., "Incorporation of Casein Phosphopeptide-Amorphous Calcium Phosphate into a Temporary Cement", Abstract 0653, 84th General Session of the IADR, Jun. 28-Jul. 1, 2006, Brisbane, Australia, 1 page.

Wright, S. et al., "Artificial Caries Inhibited with MI Paste and Two Restorative Materials", Abstract 2777, IADR, 2007, New Orleans, USA, 2 pages.

Xie, Q. et al., "Remineralization Effects of CPP-ACP and Proanthocyanidin on Artificial Root Caries", Abstract 0512, IADR, 2007, New Orleans, USA, 2 pages.

Yamaguchi, K. et al., "Effect of CPP-ACP paste on mechanical properties of bovine enamel as determined by an ultrasonic device", Journal of Dentistry, vol. No. 34, 2006, pp. 230-236.

Yamaguchi, K. et al., "Ultrasonic Determination of the Effect of Casein Phosphopeptide-Amorphous Calcium Phosphate Paste on the Demineralization of Bovine Dentin", Caries Res, vol. No. 41, 2007, pp. 204-207.

Ying, S.N. & Liu, L., "Research progress of enamel remineralization materials [J/CD]", Chin. J. Stomatol. Res. (Electronic version), vol. No. 5, Issue No. 1, 2011, pp. 94-99.

Zanatta, F. et al., "Supragingival Plaque Removal with and without Dentifrice: A Randomized Controlled Clinical Trial", Braz Dent J, vol. No. 23, Issue No. 3, 2012, pp. 235-240.

Zero, D.T., "Dentifrices, mouthwashes, and remineralization/caries arrestment strategies", BMC Oral Health, vol. No. 6, Suppl. I:S9, Jul. 2006, 13 pages.

Zero, D.T., "In situ Caries Models", Adv Dent Res, vol. No. 9, Issue No. 3, Nov. 1995, pp. 214-230.

Zhang, L. et al., "Experimental Study of Phosphopeptide in Promoting Tooth Remineralization", Chin J Dent Res., vol. No. 3, Issue No. 1, May 2000, pp. 27-30.

Zhao, Q. et al., "The remineralization for enamel lesions by casein phosphopeptide-amorphous calcium fluoride phospate in vitro", Zhonghua Kou Qiang Yi Xue Za Zhi, vol. No. 36, Issue No. 6, 2001, 8 pages.

Fernando et al., "Self-assembly of dental surface nanofilaments and remineralisation by SnF2 and CPP-ACP nanocomplexes", Sci Rep, 2019; 9: 1285.

Gurunathan D et al., "Casein phosphopeptide-amorphous calcium phosphate: a remineralizing agent of enamel", Australian Dental Journal, 2012; 57: 404-408.

Vegarud et al, "Mineral-binding milk proteins and peptides; occurrence, biochemical and technological characteristics", British Journal of Nutrition (2000), vol. 84, Suppl. 1, p. S91-S98. (Year: 2000).

White DJ . . ."A 'return' to stannous fluoride dentifrices," J Clin Dent. 1995; 6 Spec No. 29-36.

Zhang et al., "Antioxidant Properties of Casein Phosphopeptides (CPP) and Maillard-Type Conjugated Products," Antioxidants: 9 (8): 648 (Jul. 22, 2020) (14 pgs).

Non-Final Office Action on U.S. Appl. No. 17/438,299 dated Mar. 13, 2025.

Office Action issued in U.S. Appl. No. 17/438,299 dated Oct. 23, 2025.

* cited by examiner $$y = 15.441\ln(x) - 22.871$$
$$R^2 = 0.9914$$

Temperature (°C)

$$y = -0.0212x^2 + 1.6753x - 16.717$$
$$R^2 = 1$$

SEQUENCE LISTING

<160> NUMBER OF SEQ ID NOS: 4

<210> SEQ ID NO 1
<211> LENGTH: 21
<212> TYPE: PRT
<213> ORGANISM: Artificial Sequence
<220> FEATURE:
<223> OTHER INFORMATION: alphas1(59-79) phosphopeptide
<220> FEATURE:
<221> NAME/KEY: MOD_RES
<222> LOCATION: (6)..(6)
<223> OTHER INFORMATION: PHOSPHORYLATION
<220> FEATURE:
<221> NAME/KEY: MOD_RES
<222> LOCATION: (8)..(10)
<223> OTHER INFORMATION: PHOSPHORYLATION
<220> FEATURE:
<221> NAME/KEY: MOD_RES
<222> LOCATION: (17)..(17)
<223> OTHER INFORMATION: PHOSPHORYLATION

<400> SEQUENCE: 1

Gln Met Glu Ala Glu Ser Ile Ser Ser Ser Glu Glu Ile Val Pro Asn
1               5                   10                  15

Ser Val Glu Gln Lys
            20

<210> SEQ ID NO 2
<211> LENGTH: 25
<212> TYPE: PRT
<213> ORGANISM: Artificial Sequence
<220> FEATURE:
<223> OTHER INFORMATION: beta(1-25) phosphopeptide
<220> FEATURE:
<221> NAME/KEY: MOD_RES
<222> LOCATION: (15)..(15)
<223> OTHER INFORMATION: PHOSPHORYLATION
<220> FEATURE:
<221> NAME/KEY: MOD_RES
<222> LOCATION: (17)..(19)
<223> OTHER INFORMATION: PHOSPHORYLATION

<400> SEQUENCE: 2

Arg Glu Leu Glu Glu Leu Asn Val Pro Gly Glu Ile Val Glu Ser Leu
1               5                   10                  15

Ser Ser Ser Glu Glu Ser Ile Thr Arg
            20                  25

<210> SEQ ID NO 3
<211> LENGTH: 25
<212> TYPE: PRT
<213> ORGANISM: Artificial Sequence
<220> FEATURE:
<223> OTHER INFORMATION: alphas2(46-70) phosphopeptide
<220> FEATURE:
<221> NAME/KEY: MOD_RES
<222> LOCATION: (11)..(13)
<223> OTHER INFORMATION: PHOSPHORYLATION
<220> FEATURE:
<221> NAME/KEY: MOD_RES
<222> LOCATION: (16)..(16)
<223> OTHER INFORMATION: PHOSPHORYLATION

<400> SEQUENCE: 3

Asn Ala Asn Glu Glu Glu Tyr Ser Ile Gly Ser Ser Ser Glu Glu Ser
1               5                   10                  15

Ala Glu Val Ala Thr Glu Glu Val Lys
            20                  25

-continued

```
<210> SEQ ID NO 4
<211> LENGTH: 21
<212> TYPE: PRT
<213> ORGANISM: Artificial Sequence
<220> FEATURE:
<223> OTHER INFORMATION: Alphas2(1-21) phosphopeptide
<220> FEATURE:
<221> NAME/KEY: MOD_RES
<222> LOCATION: (8)..(10)
<223> OTHER INFORMATION: PHOSPHORYLATION
<220> FEATURE:
<221> NAME/KEY: MOD_RES
<222> LOCATION: (16)..(16)
<223> OTHER INFORMATION: PHOSPHORYLATION

<400> SEQUENCE: 4

Lys Asn Thr Met Glu His Val Ser Ser Ser Glu Glu Ser Ile Ile Ser
1               5                   10                  15

Gln Glu Thr Tyr Lys
            20
```

COMPOSITIONS AND METHODS FOR PROMOTING MINERALIZATION

CROSS-REFERENCE TO RELATED APPLICATIONS

This application is the U.S. National Stage of International Application No. PCT/AU2020/050236, filed Mar. 13, 2020, and claims priority to Australian provisional applications 2019900834 and 2019903859, the entire contents of each are herein incorporated by reference in their entirety.

FIELD OF THE INVENTION

The present invention relates to compositions for uses including mineralizing a dental surface, in particular tooth enamel. Methods of mineralizing hypomineralized lesions (including subsurface lesions) in the tooth enamel caused by various means including dental caries, dental erosion and fluorosis are also provided.

BACKGROUND OF THE INVENTION

Common causes of hypomineralized lesions are caries and fluorosis.

Dental caries result from the demineralization of hard tissue of the teeth usually because of fermentation of dietary sugar by dental plaque odontopathogenic bacteria. Further, restored tooth surfaces can be susceptible to further dental caries around the margins of the restoration. Dental erosion or corrosion is the loss of tooth mineral by dietary or regurgitated acids. Dental hypersensitivity is due to exposed dentinal tubules through loss of the protective mineralized layer, cementum. Dental calculus is the unwanted accretion of calcium phosphate minerals on the tooth surface. All these conditions, dental caries, dental erosion, dental hypersensitivity and dental calculus are therefore related to imbalances in the level of calcium phosphates.

Enamel fluorosis (mottling) has been recognized for nearly a century, however, the aetiological role of fluoride was not identified until 1942. The characteristic appearance of fluorosis may be differentiated from other enamel disturbances. The clinical features of fluorotic lesions of enamel (FLE) represent a continuum ranging from fine opaque lines following the perikymata, to chalky, white enamel. The presence of a comparatively highly mineralized enamel outer surface and a hypomineralized subsurface in the fluorotic lesion stimulates the incipient enamel "white spot" carious lesion. With increasing severity, both the depth of enamel involved in the lesion and the degree of hypomineralization increases. The development of fluorosis is highly dependent on the dose, duration and timing of fluoride exposure and is believed to be related to elevated serum fluoride concentrations. Chalky "white spot" lesions may also form on developing teeth in children such as after treatment with antibiotics or fever. Such lesions indicate areas of hypomineralization (i.e. too little mineralization) of the tooth enamel.

Depending on lesion severity, fluorosis has been managed clinically by restorative replacement or micro-abrasion of the outer enamel. These treatments are unsatisfactory because they involve restorations or removal of tooth tissue. What is desired is a treatment that will mineralize the hypomineralized enamel to produce a natural appearance and structure.

Specific complexes of casein phosphopeptides and amorphous calcium phosphate ("CPP-ACP", available commercially as Recaldent™) have been shown to remineralize enamel subsurface lesions in vitro and in situ.

WO 98/40406 in the name of The University of Melbourne (the contents of which are herein incorporated fully by reference) describes casein phosphopeptide-amorphous calcium phosphate complexes (CPP-ACP) and CPP-stabilized amorphous calcium fluoride phosphate complexes (CPP-ACFP), which have been produced at alkaline pH. Such complexes have been shown to prevent enamel demineralization and promote remineralization of enamel subsurface lesions in animal and human in situ caries models. Improved casein phosphopeptide-amorphous calcium phosphate complexes (CPP-ACP) and CPP-stabilized amorphous calcium fluoride phosphate complexes (CPP-ACFP) have also been described in WO2006/056013 and WO2006/135982, including preferred complexes formed at a pH of 5 to 6.5.

The CPP which are active in forming the complexes do so whether or not they are part of a full-length casein protein. Examples of active (CPP) that can be isolated after tryptic digestion of full length casein have been specified in U.S. Pat. No. 5,015,628 and include peptides Bos $\alpha_{s1}$-casein X-5P (f59-79), Bos β-casein X-4P (f1-25), Bos $\alpha_{s2}$-casein X-4P (f46-70) and Bos $\alpha_{s2}$-casein X-4P (f1-21).

While CPP-ACP and CPP-ACFP complexes are efficacious in remineralisation of hypomineralised enamel, the current methods of manufacture limit the amount of CPP-ACP or CPP-ACFP that can be used in liquid form due to the propensity of the complexes to cross-link to form a gel. The formation of a gel lowers the activity (bioavailability) of the ions required for enamel subsurface lesion remineralisation. This is a significant limitation clinically as remineralisation is a slow process and can take several months at CPP-ACP or CPP-ACFP concentrations of 10% to effect noticeable remineralisation.

There is a need to provide improved or alternative treatments for hypomineralized lesions.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

In one aspect, the present invention provides a method of mineralizing a dental surface or sub-surface comprising
contacting the dental surface or subsurface with stabilized amorphous calcium phosphate (ACP) and/or amorphous calcium fluoride phosphate (ACFP), and simultaneously or subsequently,
heating the dental surface or subsurface to which the stabilized ACP and/or ACFP has been, or is being, applied to a temperature greater than 37° C.

In another aspect, the present invention provides a method of mineralizing a dental surface or sub-surface comprising
contacting the dental surface or subsurface with a liquid composition comprising greater than 20% w/v stabilized amorphous calcium phosphate (ACP) and/or amorphous calcium fluoride phosphate (ACFP).

In another aspect, the present invention provides a method of mineralizing a dental surface or sub-surface comprising
contacting the dental surface or subsurface with a liquid composition comprising greater than 20% w/v stabilized amorphous calcium phosphate (ACP) and/or amorphous calcium fluoride phosphate (ACFP), and simultaneously or subsequently, heating the dental surface or subsurface to which the liquid composition comprising greater than 20% w/v stabilized ACP and/or ACFP has been, or is being, applied to a temperature greater than 37° C.

In a further aspect of the present invention there is provided a method for remineralizing a dental lesion, the method comprising:

contacting the hypomineralised dental surface or subsurface with a liquid composition comprising at least 40% w/w of phosphopeptide (PP)-stabilized amorphous calcium phosphate (ACP) and/or amorphous calcium fluoride phosphate (ACFP) at a pH of greater than or equal to pH 5 but less than or equal to pH 9, thereby remineralizing the dental lesion. Preferably, the liquid composition has a pH of greater than or equal to pH 6 but less than or equal to pH 8, for example greater than or equal to pH 7 but less than or equal to pH 8.

In any aspect of the invention, the method comprises heating the dental surface or subsurface to which the stabilized ACP and/or ACFP (for example, in a liquid composition) has been, or is being, applied to a temperature greater than or equal to 40° C., greater than or equal to 45° C., greater than or equal to 50° C., greater than or equal to 55° C., greater than or equal to 60° C. or greater than or equal to 65° C.

In any aspect of the invention, the method comprises heating the dental surface or subsurface to which the stabilized ACP and/or ACFP (for example, in a liquid composition) has been, or is being, applied to a temperature greater than 37° C. but equal to or less than 65° C., greater than 40° C. but equal to or less than 65° C., greater than 45° C. but equal to or less than 65° C., greater than 50° C. but equal to or less than 65° C., greater than 55° C. but equal to or less than 65° C., greater than 60° C. but equal to or less than 65° C.

In any aspect of the present invention, the liquid composition comprising greater than 20% w/v stabilized amorphous calcium phosphate (ACP) and/or amorphous calcium fluoride phosphate (ACFP) comprises greater than or equal to 25% w/v, greater than or equal to 30% w/v, greater than or equal to 35% w/v, greater than or equal to 40% w/v, greater than or equal to 45% w/v, greater than or equal to 50% w/v, greater than or equal to 55% w/v, greater than or equal to 60% w/v, greater than or equal to 65% w/v stabilized ACP and/or ACFP, greater than or equal to 70% w/v stabilized ACP and/or ACFP, or greater than or equal to 75% w/v stabilized ACP and/or ACFP.

In any aspect of the present invention, the liquid composition comprising greater than 20% w/v stabilized amorphous calcium phosphate (ACP) and/or amorphous calcium fluoride phosphate (ACFP) comprises greater than 20% w/v stabilized ACP and/or ACFP but less than 80% w/v stabilized ACP and/or ACFP, greater than 25% w/v stabilized ACP and/or ACFP but less than 80% w/v stabilized ACP and/or ACFP, greater than 30% w/v stabilized ACP and/or ACFP but less than 80% w/v stabilized ACP and/or ACFP, greater than 35% w/v stabilized ACP and/or ACFP but less than 80% w/v stabilized ACP and/or ACFP, greater than 40% w/v stabilized ACP and/or ACFP but less than 80% w/v stabilized ACP and/or ACFP, greater than 45% w/v stabilized ACP and/or ACFP but less than 80% w/v stabilized ACP and/or ACFP, greater than 50% w/v stabilized ACP and/or ACFP but less than 80% w/v stabilized ACP and/or ACFP, greater than 55% w/v stabilized ACP and/or ACFP but less than 80% w/v stabilized ACP and/or ACFP, greater than 60% w/v stabilized ACP and/or ACFP but less than 80% w/v stabilized ACP and/or ACFP, greater than 65% w/v stabilized ACP and/or ACFP but less than 80% w/v stabilized ACP and/or ACFP, greater than 70% w/v stabilized ACP and/or ACFP but less than 80% w/v stabilized ACP and/or ACFP, or greater than 75% w/v stabilized ACP and/or ACFP but less than 80% w/v stabilized ACP and/or ACFP.

In any aspect of the present invention, the liquid composition comprises greater than 40% w/w phosphopeptide (PP)-stabilized ACP and/or ACFP, greater than 45% w/w, greater than 50% w/w stabilized ACP and/or ACFP, greater than 55% w/w stabilized ACP and/or ACFP, greater than 60% w/w stabilized ACP and/or ACFP, greater than about 65% w/w stabilized ACP and/or ACFP, greater than about 70% w/w stabilized ACP and/or ACFP, or greater than about 75% w/w stabilized ACP and/or ACFP.

In any aspect of the present invention, the liquid composition comprises greater than 40% w/w phosphopeptide (PP)-stabilized ACP and/or ACFP, greater than 40% w/w stabilized ACP and/or ACFP but less than 80% w/w stabilized ACP and/or ACFP, greater than 45% w/w stabilized ACP and/or ACFP but less than 80% w/w stabilized ACP and/or ACFP, greater than 50% w/w stabilized ACP and/or ACFP but less than 80% w/w stabilized ACP and/or ACFP, greater than 55% w/w stabilized ACP and/or ACFP but less than 80% w/w stabilized ACP and/or ACFP, greater than 60% w/w stabilized ACP and/or ACFP but less than 80% w/w stabilized ACP and/or ACFP, greater than 65% w/w stabilized ACP and/or ACFP but less than 80% w/w stabilized ACP and/or ACFP, greater than 70% w/w stabilized ACP and/or ACFP but less than 80% w/w stabilized ACP and/or ACFP, or greater than 75% w/w stabilized ACP and/or ACFP but less than 80% w/w stabilized ACP and/or ACFP.

In any aspect, the liquid composition is degassed. Degassing may be by any method that forms a negative pressure above the liquid composition. Exemplary methods involve a vacuum pump or system, for example a venturi vacuum water system.

In any aspect of the present invention, the stabilized amorphous calcium phosphate (ACP) and/or amorphous calcium fluoride phosphate (ACFP) is phosphopeptide stabilized. Preferably, the phosphopeptide (as defined below) is a casein phosphopeptide.

In any aspect, the calcium ion content of the stabilised ACP or ACFP complex is greater than about 30 moles per mole of PP. Preferably, the calcium ion content is in the range of about 30 to 100 moles of calcium per mole of PP. More preferably, the calcium ion content is in the range of about 30 to about 50 moles of calcium per mole of PP.

In a preferred embodiment of each aspect of the invention, the phosphopeptide stabilized ACP or ACFP complex in the composition has tightly bound and loosely bound calcium, wherein the bound calcium in the complex is less than the tightly bound calcium in an ACP or ACFP complex formed at a pH of 7.0. Optionally, the ACP or ACFP is predominantly in a basic form.

In any aspect, the stabilised ACP complex is a stannous-associated phosphopeptide (PP) ACP complex, and the stabilised ACFP complex is a stannous-associated phosphopeptide (PP) stabilized amorphous calcium fluoride phosphate (ACFP) complex.

In any aspect, the ACP and/or ACFP complex is in the form of a casein phosphopeptide stabilized ACP and/or ACFP complex.

Preferably, the phase of the ACP is primarily (i.e. >50%) a basic phase, wherein the ACP comprises predominantly the species $Ca^{2+}$, $PO_4^{3-}$ and $OH^-$. The basic phase of ACP may have the general formula $[Ca_3(PO_4)_2]_x[Ca_2(PO_4)(OH)]$ where x≥1. Preferably x=1-5. More preferably, x=1, i.e. the two components of the formula are present in equal proportions. Accordingly, in one embodiment, the basic phase of ACP has the formula $Ca_3(PO_4)_2Ca_2(PO_4)(OH)$.

Preferably, the phase of the ACFP is a primarily (i.e. >50%) basic phase, wherein the ACFP comprises predominantly the species $Ca^{2+}$, $PO_4^{3-}$ and $F^-$. The basic phase of ACFP may have the general formula $[Ca_3(PO_4)_2]_x[Ca_2(PO_4)F]_y$, where x≥1 when y=1 or where y≥1 when x=1. Preferably, y=1 and x=1-3. More preferably, y=1 and x=1, i.e. the two components of the formula are present in equal proportions. Accordingly, in one embodiment, the basic phase of ACFP has the formula $Ca_3(PO_4)_2Ca_2(PO_4)F$.

In one embodiment, the ACP complex consists essentially of phosphopeptides, calcium, phosphate and hydroxide ions and water. Preferably, the complex further includes stannous ions.

In one embodiment, the ACFP complex consists essentially of phosphopeptides, calcium, phosphate, fluoride and hydroxide ions and water. Preferably, the complex further includes stannous ions.

In one aspect, the present invention provides a method of treating fluorosis comprising contacting a fluorotic lesion, preferably in dental enamel, with stabilized ACP and/or ACFP, and simultaneously or subsequently, heating the fluorotic lesion to which the stabilized ACP and/or ACFP has been, or is being, applied to a temperature greater than 37° C.

In another aspect, the present invention provides a method of treating fluorosis comprising contacting a fluorotic lesion, preferably in dental enamel, with a liquid composition comprising greater than 20% w/v stabilized ACP and/or ACFP.

In another aspect, the present invention provides a method of treating fluorosis comprising contacting a fluorotic lesion, preferably in dental enamel, with a liquid composition comprising greater than 20% w/v stabilized ACP and/or ACFP, and simultaneously or subsequently, heating the fluorotic lesion to which the liquid composition comprising greater than 20% w/v stabilized ACP and/or ACFP has been, or is being, applied to a temperature greater than 37° C.

In one aspect, the present invention provides a method of treating dental caries comprising contacting a caries lesion with stabilized ACP and/or ACFP, and simultaneously or subsequently, heating the caries lesion to which the stabilized ACP and/or ACFP has been, or is being, applied to a temperature greater than 37° C.

In another aspect, the present invention provides a method of treating dental caries comprising contacting a caries lesion with a liquid composition comprising greater than 20% w/v stabilized ACP and/or ACFP.

In another aspect, the present invention provides a method of treating dental caries comprising contacting a caries lesion with a liquid composition comprising greater than 20% w/v stabilized ACP and/or ACFP, and simultaneously or subsequently, heating the caries lesion to which the liquid composition comprising greater than 20% w/v stabilized ACP and/or ACFP has been, or is being, applied to a temperature greater than 37° C.

In any aspect of the present invention, a method, use or composition of the invention may be used for treating dental erosion. In this aspect, a lesion in tooth enamel caused by erosion is contacted with stabilized ACP and/or ACFP or liquid composition comprising greater than 20% w/v stabilized ACP and/or ACFP.

In any aspect of the present invention, a method, use or composition of the invention may be used for reducing white spot lesions. In this aspect, a white spot lesion, preferably on tooth enamel, is contacted with stabilized ACP and/or ACFP or liquid composition comprising greater than 20% w/v stabilized ACP and/or ACFP.

In any aspect of the present invention, a method, use or composition of the invention may be used for remineralizing a lesion in tooth enamel or dentine. In this aspect, the lesion, preferably on tooth enamel, is contacted with stabilized ACP and/or ACFP or liquid composition comprising greater than 20% w/v stabilized ACP and/or ACFP.

In any aspect of the present invention, the liquid composition comprises equal to, or greater than, about 40% w/v stabilized ACP.

In any aspect of the present invention, the liquid composition comprises equal to, or greater than, about 50% w/v stabilized ACFP.

In any aspect of the present invention, the dental surface or subsurface, or lesion (e.g. fluorotic, caries, white spot or caused by erosion), may be heated to a temperature equal to or greater than about 45° C. Preferably, the temperature does not exceed 65° C.

In any aspect of the invention, the pH of the liquid composition is less than or equal to 6. Preferably, the pH is equal to or less than 5.5. Alternatively, the pH of the liquid composition is greater than or equal to pH 5 but less than or equal to pH 9, preferably, greater than or equal to pH 6 but less than or equal to pH 8, most preferably greater than or equal to pH 7 but less than or equal to pH 8.

In one embodiment, when the % w/v of stabilized ACP and/or ACFP is greater than 20% w/v but less than 40% w/v the pH of the liquid composition is between about 5 to about 8, preferably about 5 to about 7, preferably between 5 and 7. In another embodiment, when the % w/v of stabilized ACP and/or ACFP is greater than 40% w/v the pH of the liquid composition is less than or equal to 6. Preferably, the pH is equal to or less than 5.5.

In any aspect of the invention described herein, stabilized ACP or ACFP, liquid composition comprising stabilized ACP or ACFP, and/or heat is applied to the mouth, tooth or lesion by a dental health care professional.

In any aspect of the present invention, the dental surface or subsurface, or lesion (e.g. fluorotic, caries, white spot or caused by erosion), may be heated for about 1 to 60 minutes, or for about 1 to 30 minutes.

Preferably the stabilized ACP and/or ACFP or liquid composition comprising stabilized ACP and/or ACFP are contacted with the dental surface for a period of about 1 minute to 2 hours, or 5 minutes to 60 minutes or about 10 minutes.

In any aspect, the dental surface or subsurface, or lesion, is in need of such treatment. Therefore the invention includes in addition to the steps of any method described herein a step of identifying a subject suffering fluorosis, dental caries, dentinal hypersensitivity or dental calculus, a white spot lesion; a fluorotic lesion; a caries lesion; or a lesion caused by tooth erosion.

In another aspect, the present invention provides a liquid composition comprising greater than 20% w/v stabilized ACP and/or ACFP. Preferably, the liquid composition comprising greater than 20% w/v stabilized ACP and/or ACFP comprises greater than or equal to 25% w/v, greater than or equal to 30% w/v, greater than or equal to 35% w/v, greater than or equal to 40% w/v, greater than or equal to 45% w/v, greater than or equal to 50% w/v stabilized ACP and/or ACFP, greater than or equal to 55% w/v stabilized ACP and/or ACFP, greater than or equal to 60% w/v stabilized ACP and/or ACFP, greater than or equal to 65% w/v stabilized ACP and/or ACFP, greater than or equal to 70% w/v stabilized ACP and/or ACFP, or greater than or equal to 75% w/v stabilized ACP and/or ACFP.

In this aspect of the present invention, the liquid composition may comprise greater than 20% w/v stabilized ACP and/or ACFP but less than 80% w/v stabilized ACP and/or ACFP, greater than 25% w/v stabilized ACP and/or ACFP but less than 80% w/v stabilized ACP and/or ACFP, greater than 30% w/v stabilized ACP and/or ACFP but less than 80% w/v stabilized ACP and/or ACFP, greater than 35% w/v stabilized ACP and/or ACFP but less than 80% w/v stabilized ACP and/or ACFP, greater than 40% w/v stabilized ACP and/or ACFP but less than 80% w/v stabilized ACP and/or ACFP, greater than 45% w/v stabilized ACP and/or ACFP but less than 80% w/v stabilized ACP and/or ACFP, greater than 50% w/v stabilized ACP and/or ACFP but less than 80% w/v stabilized ACP and/or ACFP, greater than 55% w/v stabilized ACP and/or ACFP but less than 80% w/v stabilized ACP and/or ACFP, greater than 60% w/v stabilized ACP and/or ACFP but less than 80% w/v stabilized ACP and/or ACFP, greater than 65% w/v stabilized ACP and/or ACFP but less than 80% w/v stabilized ACP and/or ACFP, greater than 70% w/v stabilized ACP and/or ACFP but less than 80% w/v stabilized ACP and/or ACFP, or greater than 75% w/v stabilized ACP and/or ACFP but less than 80% w/v stabilized ACP and/or ACFP.

In this aspect, the liquid composition comprises greater than 40% w/w phosphopeptide (PP)-stabilized ACP and/or ACFP, greater than 45% w/w, greater than 50% w/w stabilized ACP and/or ACFP, greater than 55% w/w stabilized ACP and/or ACFP, greater than 60% w/w stabilized ACP and/or ACFP, greater than about 65% w/w stabilized ACP and/or ACFP, greater than about 70% w/w stabilized ACP and/or ACFP, or greater than about 75% w/w stabilized ACP and/or ACFP.

In this aspect, the liquid composition comprises greater than 40% w/w phosphopeptide (PP)-stabilized ACP and/or ACFP, greater than 40% w/w stabilized ACP and/or ACFP but less than 80% w/w stabilized ACP and/or ACFP, greater than 45% w/w stabilized ACP and/or ACFP but less than 80% w/w stabilized ACP and/or ACFP, greater than 50% w/w stabilized ACP and/or ACFP but less than 80% w/w stabilized ACP and/or ACFP, greater than 55% w/w stabilized ACP and/or ACFP but less than 80% w/w stabilized ACP and/or ACFP, greater than 60% w/w stabilized ACP and/or ACFP but less than 80% w/w stabilized ACP and/or ACFP, greater than 65% w/w stabilized ACP and/or ACFP but less than 80% w/w stabilized ACP and/or ACFP, greater than 70% w/w stabilized ACP and/or ACFP but less than 80% w/w stabilized ACP and/or ACFP, or greater than 75% w/w stabilized ACP and/or ACFP but less than 80% w/w stabilized ACP and/or ACFP.

In any aspect as described herein, the liquid composition may further comprise fluoride ions, preferably free fluoride ions. The fluoride ions may be present in the liquid composition at a concentration in the range of about 200 ppm to 50,000 ppm. In a preferred embodiment, the fluoride ions are at a concentration in the range of about 2,600 ppm to about 10,000 ppm. In a further preferred embodiment, the fluoride ions in the liquid composition are at a concentration of about 8,200 ppm, or about 6,500 ppm. The fluoride ions may be present in the liquid composition at any ppm described herein, particularly the Examples. In any embodiment, the fluoride ions are at a concentration of about 2,600 ppm, 3,900 ppm, 5,200 ppm, 6,500 ppm or 7,800 ppm. Typically, the fluoride ions are at a concentration of about 2600 ppm for 20% w/v stabilized-ACP or ACFP, about 3,260 ppm for 25% w/v stabilized-ACP or ACFP, about 3,900 ppm for 30% w/v stabilized-ACP or ACFP, about 4,890 ppm for 38% stabilized-ACP or ACFP, 5,200 ppm for 40% w/v stabilized-ACP or ACFP, 6,500 ppm for 50% w/v stabilized-ACP or ACFP, about 8,200 ppm for 63% stabilized-ACP or ACFP and about 9,900 ppm for 75% stabilized-ACP or ACFP. In another embodiment, the fluoride ions are at a concentration of about 5,200 ppm for 40% w/w CPP-ACP or about 7,800 ppm for 60% w/w CPP-ACP. Preferably, the stabilized-ACP and/or ACFP is phosphopeptide stabilized. Preferably, the phosphopeptide is a casein phosphopeptide.

Any composition described herein can be used in any one of the methods described herein. The composition is a physiologically acceptable composition as described herein.

In another aspect, the present invention provides a liquid composition comprising greater than 20% w/v stabilized ACP and/or ACFP for use in:
mineralizing a dental surface or subsurface, or any lesion as described herein; or
treating or preventing one or more of each of dental caries, tooth decay, dental erosion, white spot lesions and fluorosis.

In a further aspect there is provided the use of a liquid composition comprising greater than 20% w/v stabilized ACP and/or ACFP in the manufacture of a composition or medicament for the mineralizing a dental surface or subsurface, or treatment and/or prevention of one or more of dental caries, tooth decay, dental erosion and fluorosis.

In a further aspect, there is provided a use of a phosphopeptide (PP)-stabilized amorphous calcium phosphate (ACP) and/or amorphous calcium fluoride phosphate (ACFP) in the manufacture of a product comprising or consisting of a liquid composition for remineralizing a dental surface or subsurface,
the liquid composition comprising at least 40% w/w of said phosphopeptide (PP)-stabilized amorphous calcium phosphate (ACP) and/or amorphous calcium fluoride phosphate (ACFP) at a pH of greater than or equal to pH 5 but less than or equal to pH 9, In one embodiment, the product is a cosmetic product.

The invention also relates to a kit for the treatment or prevention of one or more of dental caries, fluorosis and dental erosion, or mineralizing a dental surface or subsurface or lesion as described herein comprising (a) a liquid composition comprising greater than 20% w/v stabilized ACP and/or ACFP, and (b) a heat source. Desirably, the kit further includes instructions for their use in any method or use described herein. The instructions may describe the use of the kit to treat or prevent one or more of each of dental caries, tooth decay, dental erosion and fluorosis. In one embodiment, the liquid composition is present in suitable amounts for treatment of a patient. Preferably, the stabilized ACP and/or ACFP is phosphopeptide (PP)-stabilized. Preferably, the phosphopeptide (as defined below) is a casein phosphopeptide. Preferably, the ACP or ACFP is in the form of a casein phosphopeptide stabilized ACP or ACFP complex.

The composition or kit of the invention may further include a source of fluoride ions. The fluoride ions may be from any suitable source. A source of fluoride ions may include free fluoride ions or fluoride salts. Examples of sources of fluoride ions include, but are not limited to the following: sodium fluoride, sodium monofluorophosphate, stannous fluoride, sodium silicofluoride, silver fluoride, amine fluoride or any metal ion fluoride salt. A source of fluoride ions may be a hypofluorite. These sources of fluoride ions may be provided in solution (typically an aqueous solution), or a suspension.

In another aspect, the present invention provides a method or process for preparing a liquid composition comprising greater than 20% w/v stabilized ACP and/or ACFP, the method or process comprising or consisting of:

mixing a solvent and a powder comprising or consisting of stabilized-ACP and/or ACFP, and maintaining the pH below 7. Preferably, the pH is maintained at, or below, 6, preferably the pH is maintained at, or below, 5.5.

In another aspect, the present invention provides a method or process for preparing a liquid composition comprising greater than 20% w/v stabilized ACP and/or ACFP, the method or process comprising or consisting of:

mixing a solvent and a powder comprising or consisting of stabilized ACP and/or ACFP, and lowering the pH below 7. Preferably, the pH is lowered to, or below, 6, preferably 5.5. Typically, the pH is maintained below, 7, more preferably the pH is maintained at, or below, 6, even more preferably 5.5.

In another aspect, the present invention provides a method or process for preparing a liquid composition comprising greater than 20% w/v stabilized ACP and/or ACFP, the method or process comprising or consisting of:

mixing a fluoride containing solution and a powder comprising or consisting of stabilized ACP and/or ACFP, and adjusting the pH to between 6.5 and 8. Preferably, the pH is adjusted to about pH 7.8. Preferably, the pH is adjusted with HCl.

In this aspect, the method further comprises the step of mixing the solution for at least about 10 minutes, at least about 20 minutes, or at least about 30 minutes after the pH is adjusted.

In this aspect, the method further comprises the step of degassing the liquid composition.

In any aspect, the step of mixing a solvent and a powder comprising or consisting of PP stabilized ACP and/or ACFP, comprises adding the solvent to the powder. Alternatively, the step comprises adding the powder to the solvent.

In any method or process for preparing a liquid composition as described herein, the method or process further comprises the step of degassing the liquid composition. Degassing may be by any method that forms a negative pressure above the liquid composition, including methods described herein.

In any method or process for preparing a liquid composition as described herein, the method or process further comprises a step of mixing the liquid composition with a solution comprising fluoride ions.

In another aspect, the present invention provides a method or process for preparing a liquid composition comprising greater than 20% w/v stabilized ACP and/or ACFP, the method or process comprising or consisting of the steps as described in Example 2 or 4 herein.

In any aspect, the present invention provides a method or process that further comprises the following steps to prepare a powder comprising or consisting of stabilized-ACP and/or ACFP:

admixing one or more solutions comprising phosphopeptides, calcium ions, phosphate ions, hydroxide ions and optionally fluoride ions, while maintaining the pH at about 7.0 or above, preferably about 9, to form a solution comprising stabilized-ACP and/or ACFP, and drying the solution comprising stabilized-ACP and/or ACFP, thereby forming a powder comprising or consisting of stabilized-ACP and/or ACFP. Preferably drying is spray drying or freeze drying.

In one embodiment, the method or process further comprises the steps;

filtering the solution comprising stabilized-ACP and/or ACFP, prior to drying, to form a retentate, wherein the retentate is subsequently dried to form powder comprising or consisting of stabilized-ACP and/or ACFP.

In another aspect, the present invention provides a method or process for preparing a liquid composition comprising at least 40% w/w PP stabilized ACP and/or ACFP, the method or process comprising or consisting of:

mixing a solvent and a powder comprising or consisting of PP stabilized ACP and/or ACFP, and lowering the pH below 9, preferably 8. Preferably the solvent comprises fluoride.

In this aspect, the method further comprises a step of stirring the liquid composition after the pH is lowered. Preferably, the stirring occurs for at least 5, 10, 15, 20, 25 or 30 minutes.

In this aspect, the liquid composition is degassed to remove trapped air bubbles, preferably by placing the solution under vacuum, most preferably for 24 hours.

In another aspect, the present invention provides a method or process for preparing a liquid composition comprising at least 40% w/w, preferably 60% w/w, PP stabilized ACP and/or ACFP, the method or process comprising or consisting of the steps as described in Example 4 herein.

In any method or process for preparing a liquid composition comprising greater than 20% w/v or greater than 40% w/w stabilized ACP and/or ACFP, the solvent is water.

In any method or process for preparing a liquid composition comprising greater than 20% w/v stabilized ACP and/or ACFP, the pH is lowered or maintained using 1-10M HCl, or 11M HCl.

In any aspect, the method or process for preparing a liquid composition comprising greater than 20% w/v stabilized ACP and/or ACFP, may be for preparing a liquid composition comprising equal to or greater than 25% w/v, 30% w/v, 35% w/v, 40% w/v, 45% w/v, 50% w/v, 55% w/v, 60% w/v, 65% w/v, 70% w/v, 75% w/v or 80% w/v stabilized ACP and/or ACFP.

In any method or process for preparing a liquid composition comprising greater than 20% w/v stabilized ACP and/or ACFP, the stabilized ACP or ACFP is CPP-ACP or CPP-ACFP as described herein.

In any method or process for preparing a liquid composition comprising greater than 20% w/v stabilized ACP and/or ACFP, the liquid composition is for use in any method of dental treatment, preferably those described herein (e.g. mineralizing a dental surface or sub-surface).

In another aspect, the present invention provides a liquid composition comprising greater than 20% w/v stabilized ACP and/or ACFP prepared by a method or process described herein.

Further aspects of the present invention and further embodiments of the aspects described in the preceding paragraphs will become apparent from the following description, given by way of example and with reference to the accompanying drawings.

DETAILED DESCRIPTION OF THE EMBODIMENTS

Figure 1:
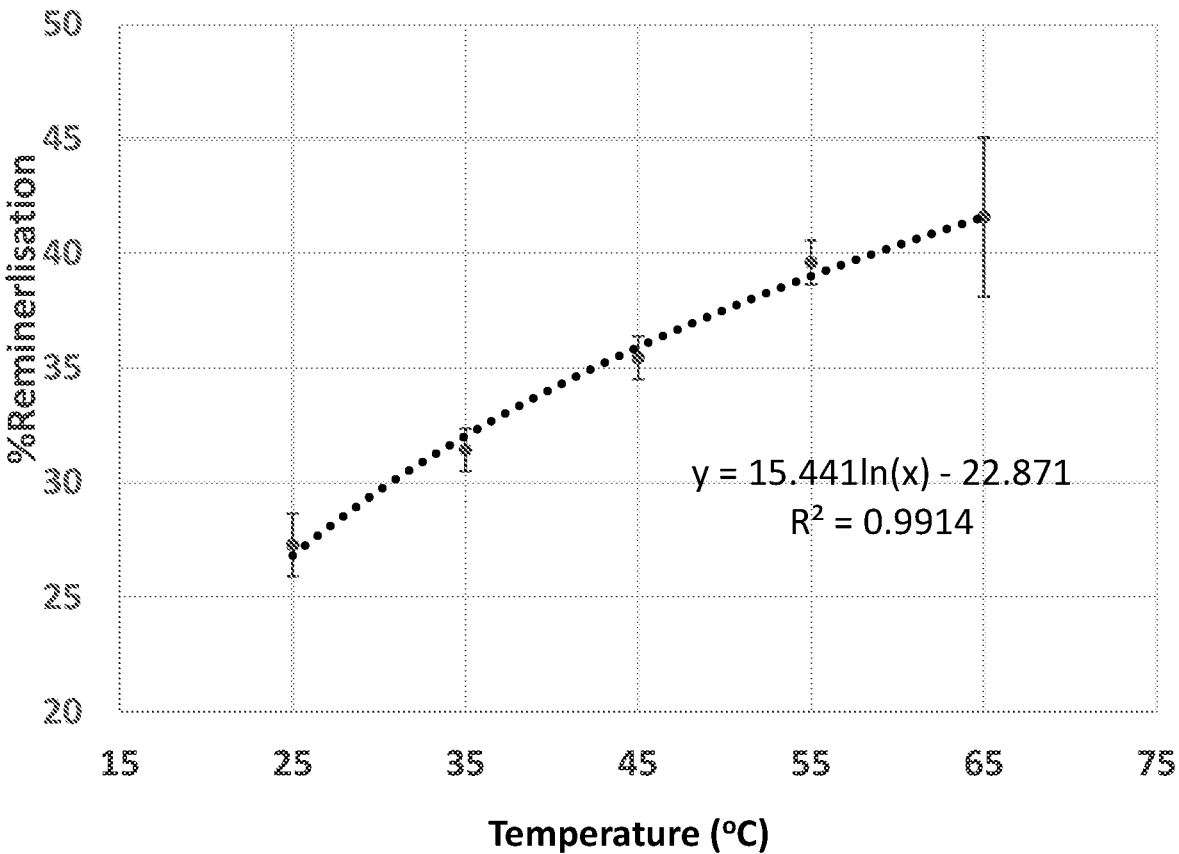
FIG. 1: Effect of Temperature on Remineralisation of Enamel Subsurface Lesions in vitro.

It will be understood that the invention disclosed and defined in this specification extends to all alternative combinations of two or more of the individual features mentioned or evident from the text or drawings. All of these different combinations constitute various alternative aspects of the invention.

Further aspects of the present invention and further embodiments of the aspects described in the preceding paragraphs will become apparent from the following description, given by way of example and with reference to the accompanying drawings.

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described.

All of the patents and publications referred to herein are incorporated by reference in their entirety.

For purposes of interpreting this specification, terms used in the singular will also include the plural and vice versa.

As used herein, except where the context requires otherwise, the term "comprise" and variations of the term, such as "comprising", "comprises" and "comprised", are not intended to exclude further additives, components, integers or steps. As used herein, except where the context requires otherwise, "comprise" and "include" can be used interchangeably.

An aspect of an invention described herein is based on the surprising finding that it is possible to achieve a composition of a high concentration of stabilized ACP and/or ACFP and the composition still maintain a liquid state (i.e. does not form a gel). Prior to the present invention it was thought that high concentrations of phosphopeptide-stabilized ACP and/or ACFP would result in the composition forming a gel or paste, and all liquid compositions described to date had relatively low concentrations of phosphopeptide-stabilized ACP and/or ACFP. The unexpected property of a high concentration composition of phosphopeptide-stabilized ACP and/or ACFP maintaining a liquid state prior to application to a dental surface or subsurface allows more rapid penetrance into a hypomineralized site. Without being bound by any theory or mode of action, it is believed that a higher concentration of stabilized ACP and/or ACFP can be achieved in the lesion which results in more rapid remineralization and to a greater extent. This provides the advantage that the high concentration liquid composition can be applied by a dental professional directly onto a lesion allowing more extensive remineralization to occur compared to in-home application of low concentration compositions, such as pastes or mousses.

Further, a separate aspect of an invention described herein is based on the surprising finding that heating the dental surface or subsurface at the same time as, or subsequent to, the application of stabilized ACP and/or ACFP increases the extent of mineralization, even up to relatively high temperatures.

Finally, a combination of both high concentration liquid compositions with heating of the dental surface to which the stabilized ACP and/or ACFP has been or is being applied, provides for extensive and rapid remineralization.

Any heat source may be used in a method or use of the invention to heat the dental surface or subsurface. Heat sources that emit light or radiation and are suitable for use in dental applications are known in the art. Specific examples include dental curing lights, for example a 10 W high-power blue light LED such as X-Cure by Guilin Woodpecker Medical Instrument Co. Ltd.

As used herein % w/v may be taken to be equivalent to g/100 ml.

As used herein, "stabilized-ACP or ACFP" and "stabilized-ACP or ACFP complex" are used interchangeably.

Figure 2:
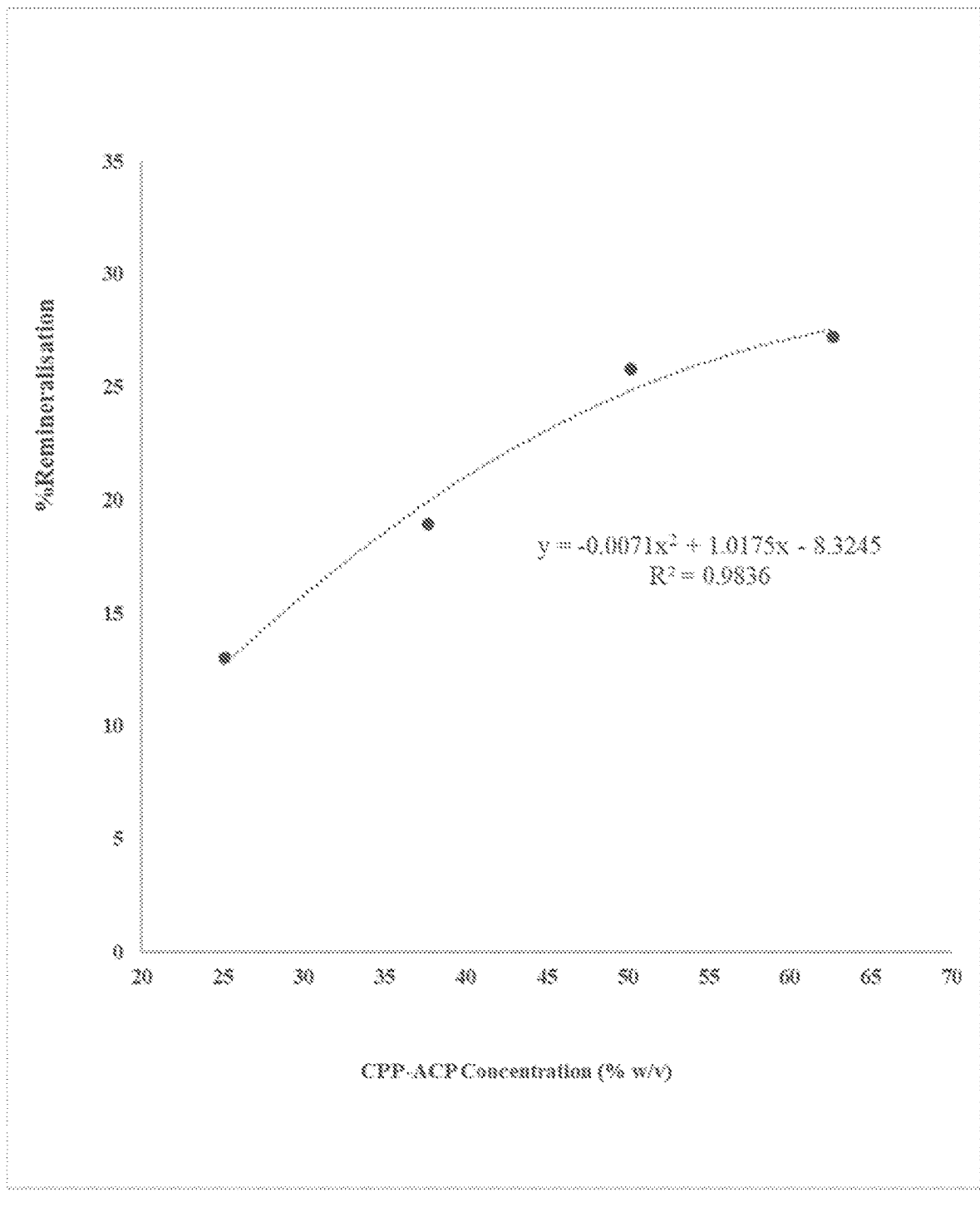
FIG. 2: Remineralisation by high concentrations of CPP-ACP in the presence of fluoride.
Figure 3:
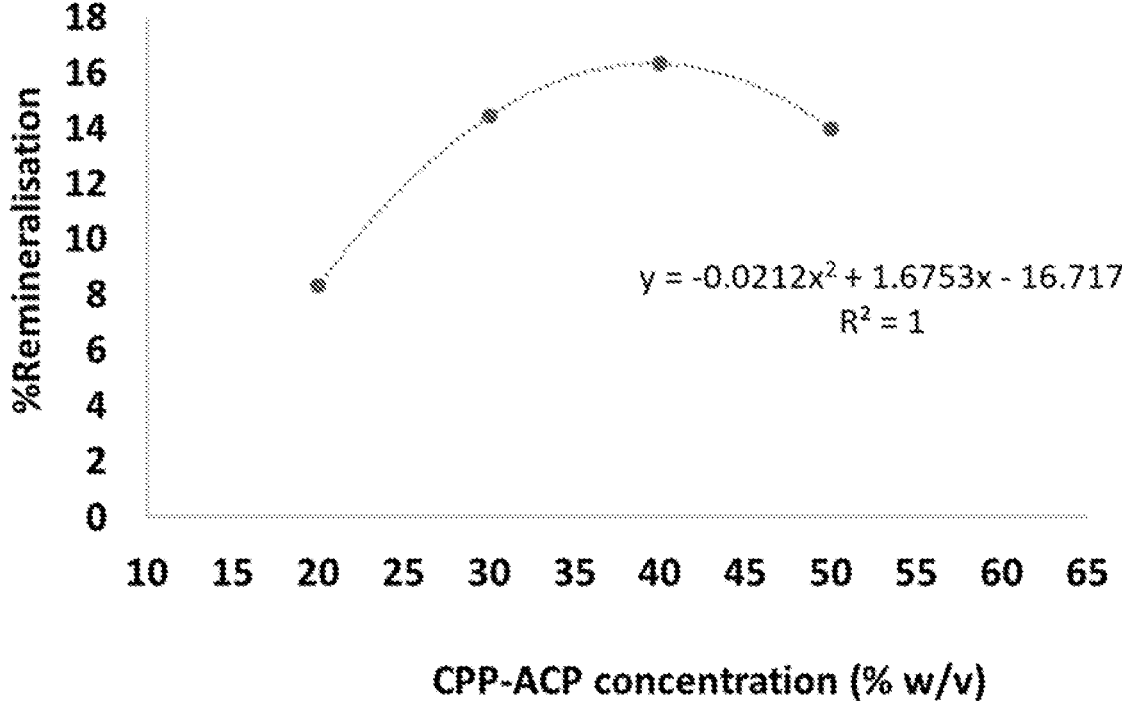
FIG. 3: Remineralisation by high concentrations of CPP-ACP.

A stabilized-ACP or ACFP complex as described in the current specification may be the "closed" complexes are shown in FIG. 2 of Cross et al., 2007.

A stabilized-ACP or ACFP as referred to herein include a stabilized-ACP or ACFP as described in WO2006/056013 (PCT/AU2005/001781) the contents of which are incorporated by reference.

In a preferred embodiment, the phosphopeptide stabilised amorphous calcium phosphate (ACP) or amorphous calcium fluoride phosphate (ACFP) complex has tightly bound and loosely bound calcium, wherein the bound calcium in the complex is less than the tightly bound calcium in an ACP or ACFP complex formed at a pH of 7.0. Optionally, the ACP or ACFP is predominantly in a basic form.

A stabilized-ACP or ACFP complex as referred to herein include a stabilized-ACP or ACFP complex formed at a pH of below 7.0. Preferably the complex is formed at a pH in the range of about 5.0 up to but below 7.0. More preferably the complex is formed at a pH range of about 5.0 to about 6.0. In a preferred embodiment, the complex is formed at a pH of about 5.5. Preferably, the ACP or ACFP in the complex is predominantly in a basic form.

A stabilized-ACP may be produced by a method comprising the steps of:
  (i) obtaining a solution comprising at least one phosphopeptide and;
  (ii) admixing solutions comprising calcium ions, phosphate ions and hydroxide ions, while maintaining the pH at about 5.5 to 9.

In one embodiment, the pH is maintained at about 7.0 or below.

A stabilised ACFP may be produced by a method comprising the steps of:
  (i) obtaining a solution comprising at least one phosphopeptide and;
  (ii) admixing solutions comprising calcium ions, phosphate ions, hydroxide ions and fluoride ions, while maintaining the pH at about 5.5 to 9.

In one embodiment, the pH is maintained at about 7.0 or below.

A phosphopeptide stabilised amorphous calcium phosphate (ACP) or amorphous calcium fluoride phosphate (ACFP) complex may also include wherein the ACP in the complex has tightly bound and loosely calcium, wherein the tightly bound calcium in the complex is less than the tightly bound calcium in an ACP or ACFP complex formed at a pH of 7.0 and the ACP or ACFP is predominantly in a basic form, obtainable or obtained by a method comprising:

a) admixing a first solution comprising calcium ions, a second solution comprising phosphate ions, and optionally a third solution comprising fluoride ions, to a solution comprising phosphopeptides and a solvent with a pH of from about 5 up to but below 7; and b) maintaining the pH of the solution at about 5.0 up to but below 7.0 during the admixing by adding hydroxide ions.

"Tightly" and "loosely" bound calcium and phosphate in ACP or ACFP can be determined using analytical ultrafiltration. Briefly, the solution of phosphopeptide, calcium, phosphate and optionally fluoride admixed while maintaining the pH at about 7.0 or below can be first filtered through a 0.1 micron filter to remove free calcium and phosphate that is not associated with the complexes. This free calcium and phosphate is present in the filtrate and discarded. Any free calcium or phosphate that is not associated in any way with the complexes would not be bioavailable, i.e. delivered by the phosphopeptide to the tooth. The retentate from the 0.1 micron filtration can be further analyzed by centrifugation through a 3000 mw cut-off filter at 1,000 g for 15 min. The resulting filtrate contains calcium and phosphate that is loosely bound or associated with the complexes. At this centrifugal force calcium and phosphate that is not tightly bound to the complexes are released and move to into the filtrate. The Ca and Pi that is tightly bound in the complexes is retained in the retentate. The amount of tightly bound Ca and Pi in the retentate can then be determined by subtracting the amount of Ca and Pi in the filtrate from the total amount of Ca and Pi in the retentate of the 0.1 micron filtration.

A stabilized-ACP or ACFP complex as referred to herein include a stabilized-ACP or ACFP complex as described in WO2006/135982 (PCT/AU2006/000885) the contents of which are incorporated by reference.

A "superloaded" phosphopeptide or phosphoprotein (PP) stabilized-amorphous calcium phosphate (ACP) or amorphous calcium fluoride phosphate (ACFP) complex. The complex may be formed at any pH (e.g. 3-10). Preferably the phosphopeptide includes the sequence -A-B-C-, where A is a phosphoamino acid, preferably phosphoserine, B is any amino acid including a phosphoamino acid and C is glutamic acid, aspartic acid or a phosphoamino acid. The phosphoamino acid may be phosphoserine. The PP is superloaded with calcium and phosphate ions. The calcium ions may be in the range 30-1000 mole Ca per mole of PP, or in the range of 30-100 or 30-50 mole Ca per mole of PP. In another embodiment, the mole Ca per mole of PP is at least 25, 30, 35, 40, 45 or 50.

The phosphopeptide or phosphoprotein (PP) stabilized amorphous calcium phosphate or amorphous calcium fluoride phosphate complex may have a calcium ion content greater than about 30 moles of calcium per mole of PP. In a preferred embodiment, the calcium ion content is in the range of about 30 to 100 moles of calcium per mole of PP. More preferably, the calcium ion content is in the range of about 30 to 10 about 50 moles of calcium per mole of PP.

The phosphopeptide or phosphoprotein (PP) stabilized-amorphous calcium phosphate (ACP) or amorphous calcium fluoride phosphate (ACFP) complex may be produced by a method comprising the steps of:

(i) obtaining solutions comprising calcium, inorganic phosphate and fluoride (optional); and (ii) admixing (i) with a solution comprising PP-ACP.

In a preferred embodiment, the PP is casein phosphopeptide (CPP).

The PP stabilized ACP and/or ACFP complex may further include at least an equal amount by weight of calcium phosphate. Preferably the calcium phosphate is CaHPO$_4$. Preferably, the calcium phosphate (e.g. CaHPO$_4$) is dry blended with the PP stabilized ACP and/or ACFP complex. In a preferred embodiment, the PP-ACP and/or PP-ACFP complex: calcium phosphate ratio is about 1:1-50, more preferably about 1:1-25, more preferably about 1:5-15. In one embodiment, the PP-ACP and/or PP-ACFP complex: calcium phosphate ratio is about 1:10.

The oral care formulation that includes a phosphopeptide or phosphoprotein (PP) stabilized amorphous calcium phosphate (ACP) and/or amorphous calcium fluoride phosphate (ACFP) complex having a calcium ion content greater than about 30 moles of calcium per mole of PP when used in the oral cavity may be produced by a method including the steps of:

(i) obtaining a powder including a PP-ACP and/or PP-ACFP complex;

(ii) dry blending with an effective amount of calcium phosphate; and (iii) formulating the dry blended PP-ACP and/or PP-ACFP and calcium phosphate mixture into an oral care formulation.

Preferably, the form of calcium phosphate for dry blending is any soluble calcium phosphate including, but not limited to, CaHPO$_4$, Ca$_2$HPO$_4$ and calcium lactate.

A composition as described herein may further include free fluoride ions. The fluoride ions may be from any suitable source. A source of fluoride ions may include free fluoride ions or fluoride salts. Examples of sources of fluoride ions include, but are not limited to the following: sodium fluoride, sodium monofluorophosphate, stannous fluoride, sodium silicofluoride and amine fluoride. These may be provided in solution (typically an aqueous solution), or a suspension.

The fluoride ions are preferably present in the composition in an amount greater than 1 ppm. More preferably, the amount is more than 3 ppm. In another embodiment, it is preferably more than 10 ppm. In typical embodiments described below, the amount may be several hundred or thousand ppm. Typically, the free fluoride ions are in the range of 1000 ppm to 50,000 ppm F. The ppm F may be any amount or concentration described herein. The fluoride content is typically measured as a ppm in oral compositions in the manner commonly used in the art. Where the fluoride is provided from a source with the stabilized ACP, the ppm refers to the concentration of the fluoride in that source, typically a solution or suspension of bioavailable fluoride.

A stannous-associated ACP or ACFP complex as referred to herein include any described in PCT/AU2014/050447, the entire contents of which are incorporated by reference in its entirety.

A composition as described herein for use in a method of use of the invention may include a stannous-associated ACP or ACFP complex. The composition may include 2% CPP-ACP and 290 ppm fluoride with 220 ppm fluoride as stannous fluoride and 70 ppm as sodium fluoride.

"Phosphopeptide" in the context of the description of this invention means an amino acid sequence in which at least one amino acid is phosphorylated. Preferably, the phosphopeptide includes one or more of the amino acid sequence -A-B-C-, where A is a phosphoamino residue, B is any amino acyl residue including a phosphoamino residue and C is selected from a glutamyl, aspartyl or phosphoamino residue. Any of the phosphoamino residues may independently be a phosphoseryl residue. B is desirably a residue the side-chain of which is neither relatively large nor hydrophobic. It may be Gly, Ala, Val, Met, Leu, Ile, Ser, Thr, Cys, Asp, Glu, Asn, Gln or Lys.

In another embodiment, at least two of the phosphoamino acids in the sequence are preferably contiguous. Preferably the phosphopeptide includes the sequence A-B-C-D-E, where A, B, C, D and E are independently phosphoserine, phosphothreonine, phosphotyrosine, phosphohistidine, glutamic acid or aspartic acid, and at least two, preferably three, of the A, B, C, D and E are a phosphoamino acid. In a preferred embodiment, the phosphoamino acid residues are phosphoserine, most preferably three contiguous phosphoserine residues. It is also preferred that D and E are independently glutamic or aspartic acid.

In one embodiment, the ACP or ACFP is stabilized by a casein phosphopeptide (CPP), which is in the form of intact casein or fragment of the casein, and the complex formed preferably has the formula $[CPP(ACP)_8]_n$ or $[(CPP)(ACFP)_8]_n$ where n is equal to or greater than 1, for example 6. The complex formed may be a colloidal complex, where the core particles aggregate to form large (e.g. 100 nm) colloidal particles suspended in water. Thus, the PP can be a casein protein or a phosphopeptide.

The PP may be from any source; it may be present in the context of a larger polypeptide, including a full length casein polypeptide, or it may be isolated by tryptic or other enzymatic or chemical digestion of casein, or other phosphoamino acid rich proteins such as phosphitin, or by chemical or recombinant synthesis, provided that it comprises the sequence -A-B-C- or A-B-C-D-E as described above. The sequence flanking this core sequence may be any sequence. However, those flanking sequences in $\alpha_{s1}(59\text{-}79)$, $\beta(1\text{-}25)$, $\alpha_{s2}(46\text{-}70)$ and $\alpha_{s2}(1\text{-}21)$ are preferred. The flanking sequences may optionally be modified by deletion, addition or conservative substitution of one or more residues. The amino acid composition and sequence of the flanking region are not critical.

Examples of conservative substitutions are shown in Table A below.

TABLE A

| Original Residue | Exemplary Conservative Substitution | Preferred Conservative Substitution |
|---|---|---|
| Ala | Val, Leu, Ile | Val |
| Asn | Gln Lys His Phe | Gln |
| Gln | Asn | Asn |
| Gly | Pro | Pro |
| Ile | Leu, Val, Met, Ala, Phe | Leu |
| Leu | Ile, Val, Met, Ala, Phe | Ile |
| Lys | Arg, Gln, Asn | Arg |
| Phe | Leu, Val, Ile, Ala | Leu |
| Pro | Gly | Gly |
| Ser | Thr | Thr |
| Val | Ile, Leu, Met, Phe, Ala | Leu |
| Asp | Glu | Glu |
| Thr | Ser | Ser |
| Trp | Tyr | Tyr |
| Tyr | Trp Phe Thr Ser | Phe |

The flanking sequences may also include non-naturally occurring amino acid residues. Commonly encountered amino acids which are not encoded by the genetic code, include:

2-amino adipic acid (Aad) for Glu and Asp;

2-aminopimelic acid (Apm) for Glu and Asp;

2-aminobutyric (Abu) acid for Met, Leu, and other aliphatic amino acids;

2-aminoheptanoic acid (Ahe) for Met, Leu and other aliphatic amino acids;

2-aminoisobutyric acid (Aib) for Gly;

cyclohexylalanine (Cha) for Val, and Leu and Ile;

homoarginine (Har) for Arg and Lys;

2,3-diaminopropionic acid (Dpr) for Lys, Arg and His;

N-ethylglycine (EtGly) for Gly, Pro, and Ala;

N-ethylasparigine (EtAsn) for Asn, and Gln;

Hydroxyllysine (Hyl) for Lys;

allohydroxyllysine (AHyl) for Lys;

3-(and 4) hydroxyproline (3Hyp, 4Hyp) for Pro, Ser, and Thr;

alloisoleucine (Alle) for Ile, Leu, and Val;

ρ-amidinophenylalanine for Ala;

N-methylglycine (MeGly, sarcosine) for Gly, Pro, Ala.

N-methylisoleucine (Melle) for Ile;

Norvaline (Nva) for Met and other aliphatic amino acids;

Norleucine (Nle) for Met and other aliphatic amino acids;

Ornithine (Orn) for Lys, Arg and His;

Citrulline (Cit) and methionine sulfoxide (MSO) for Thr, Asn and Gln;

N-methylphenylalanine (MePhe), trimethylphenylalanine, halo (F, Cl, Br and I) phenylalanine, triflourylphenylalanine, for Phe.

In one embodiment, the PP is one or more phosphopeptides selected from the group consisting of $\alpha_{s1}(59\text{-}79)$ [1], $\beta(1\text{-}25)$ [2], $\alpha_{s2}(46\text{-}70)$ [3] and $\alpha_{s2}(1\text{-}21)$ [4]:

[1]

(SEQ ID NO: 1)

$Gln^{59}$-Met-Glu-Ala-Glu-Ser(P)-Ile-Ser(P)-Ser(P)-Ser(P)-Glu-Glu-Ile-Val-Pro-Asn-Ser(P)-Val-Glu-Gln-$Lys^{79}$ $\alpha_{s1}(59\text{-}79)$

[2]

(SEQ ID NO: 2)

$Arg^1$-Glu-Leu-Glu-Glu-Leu-Asn-Val-Pro-Gly-Glu-Ile-Val-Glu-Ser(P)-Leu-Ser(P)-Ser(P)-Ser(P)-Glu-Glu-Ser-Ile-Thr-$Arg^{25}$ $\beta(1\text{-}25)$

[3]

(SEQ ID NO: 3)

$Asn^{46}$-Ala-Asn-Glu-Glu-Glu-Tyr-Ser-Ile-Gly-Ser(P)-Ser(P)-Ser(P)-Glu-Glu-Ser(P)-Ala-Glu-Val-Ala-Thr-Glu-Glu-Val-$Lys^{70}$ $\alpha_{s2}(46\text{-}70)$

[4]

(SEQ ID NO: 4)

$Lys^1$-Asn-Thr-Met-Glu-His-Val-Ser(P)-Ser(P)-Ser(P)-Glu-Glu-Ser-Ile-Ile-Ser(P)-Gln-Glu-Thr-Tyr-$Lys^{21}$ $\alpha_{s2}(1\text{-}21)$.

In certain preferred forms of the invention a liquid composition may a mouthwash, rinse or spray. In such a preparation the vehicle is typically a water-alcohol mixture desirably including a humectant as described below. Generally, the weight ratio of water to alcohol is in the range of from about 1:1 to about 20:1. The total amount of water-alcohol mixture in this type of preparation is typically in the range of from about 70 to about 99.9% by weight of the preparation. The alcohol is typically ethanol or isopropanol. Ethanol is preferred.

It will be understood that, as is conventional, the oral preparations will usually be sold or otherwise distributed in suitable labelled packages. Thus, a jar of mouth rinse will have a label describing it, in substance, as a mouth rinse or mouthwash and having directions for its use.

Organic surface-active agents may be used in the compositions of the present invention to achieve increased prophylactic action, assist in achieving thorough and complete dispersion of the active agent throughout the oral cavity, and render the instant compositions more cosmetically acceptable. The organic surface-active material is preferably anionic, non-ionic or ampholytic in nature and preferably does not interact with the active agent. It is preferred to employ as the surface-active agent a detersive material which imparts to the composition detersive and foaming properties. Suitable examples of anionic surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkylsulfo-acetates, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine which should be substantially free from soap or similar higher fatty acid material. The use of these sarconite compounds in the oral compositions of the present invention is particularly advantageous since these materials exhibit a prolonged marked effect in the inhibition of acid formation in the oral cavity due to carbohydrates breakdown in addition to exerting some reduction in the solubility of tooth enamel in acid solutions. Examples of water-soluble non-ionic surfactants suitable for use are condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of poly (ethylene oxide) with fatty acids, fatty alcohols, fatty amides, polyhydric alcohols (e.g. sorbitan monostearate) and polypropyleneoxide (e.g. Pluronic materials).

The surface active agent is typically present in amount of about 0.1-5% by weight. It is noteworthy, that the surface active agent may assist in the dissolving of the active agent of the invention and thereby diminish the amount of solubilizing humectant needed.

Various other materials may be incorporated in the oral preparations of this invention such as whitening agents, preservatives, silicones, chlorophyll compounds and/or ammoniated material such as urea, diammonium phosphate, and mixtures thereof. These adjuvants, where present, are incorporated in the preparations in amounts which do not substantially adversely affect the properties and characteristics desired.

Any suitable flavouring or sweetening material may also be employed. Examples of suitable flavouring constituents are flavouring oils, e.g. oil of spearmint, peppermint, wintergreen, *sassafras*, clove, sage, *eucalyptus*, marjoram, cinnamon, lemon, and orange, and methyl salicylate. Suitable sweetening agents include sucrose, lactose, maltose, sorbitol, xylitol, sodium cyclamate, perillartine, AMP (aspartyl phenyl alanine, methyl ester), saccharine, and the like.

Suitably, flavour and sweetening agents may each or together comprise from about 0.1% to 5% more of the preparation.

In another embodiment, the compositions of the invention as described herein do not include a phosphate buffer and/or a calcium chelator. For example, any dentifrice described herein may not include a phosphate buffer and/or a calcium chelator.

In an embodiment of the present invention there is provided a composition, wherein the composition does not include a phosphate buffer and/or calcium chelator.

In another embodiment, the compositions of the invention as described herein do not include a viscosity regulator, or a viscosity regulator at 0.5 to 50%.

In another embodiment, the compositions of the invention as described herein do not include sodium carboxymethyl-cellulose, or 0.01 to 10% sodium carboxymethylcellulose having the esterification degree of 0.7 to 1.0.

In one embodiment, the active components of the composition consist essentially of the stabilized ACP or ACFP complexes.

It will be clearly understood that, although this specification refers specifically to applications in humans, the invention is also useful for veterinary purposes. Thus in all aspects the invention is useful for domestic animals such as cattle, sheep, horses and poultry; for companion animals such as cats and dogs; and for zoo animals.

The invention also provides a kit comprising stabilized amorphous calcium phosphate (ACP) and/or stabilized amorphous calcium fluoride phosphate (ACFP) said kit being adapted for use in the above described methods.

The invention also provides a kit comprising a liquid composition as described herein.

In any aspect, the kit may further comprise a label or package insert with instructions for use in any method described herein.

The kit may include:
    a container holding a composition comprising stabilized amorphous calcium phosphate (ACP) and/or stabilized amorphous calcium fluoride phosphate (ACFP);
    a label or package insert with instructions for use.

In certain embodiments the kit may contain one or more further active principles or ingredients for treatment or prevention of a disease or condition as described herein.

The kit may comprise a container and a label or package insert on or associated with the container. Suitable containers include, for example, bottles, vials, syringes, blister pack, etc. The containers may be formed from a variety of materials such as glass or plastic. The container holds a therapeutic composition which is effective for treating the condition and may have a sterile access port (for example the container may be an intravenous solution bag or a vial having a stopper pierceable by a hypodermic injection needle). The label or package insert indicates that the therapeutic composition is used for treating the condition of choice. In one embodiment, the label or package insert includes instructions for use and indicates that the therapeutic composition can be used for treatment of the given condition.

The kit may comprise (a) a liquid composition as described herein; and (b) a second container with a second active principle or ingredient contained therein. The kit in this embodiment of the invention may further comprise a package insert indicating that the composition and other active principle can be used to treat a condition as described herein. Alternatively, or additionally, the kit may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It will be understood that the invention disclosed and defined in this specification extends to all alternative com- After remineralization the enamel blocks were embedded, sectioned and subjected to transverse microradiography and densitometric image analysis as previously described by Reynolds (1997 *J Dent Res*, supra) to determine percent mineral content gain (% Remineralization). FIG. 1 shows the direct correlation between increasing temperature and increasing amount of remineralization.

TABLE 1

| Results of the Effect of Temperature on Remineralisation of Enamel Subsurface Lesions | | | | | |
|---|---|---|---|---|---|
| | LDd | LDd – LDr | ΔZd | ΔZd – ΔZr | % R |
| 25° C. | 110.62 ± 10.11 | 10.16 ± 3.29 | 3138.78 ± 568.20 | 856.66 ± 160.90$^{abc}$ | 27.30 ± 1.36$^{abcd}$ |
| 35° C. | 107.28 ± 6.38 | 11.85 ± 4.43 | 2703.38 ± 610.76 | 844.06 ± 194.21$^{de}$ | 31.30 ± 1.14$^{aefg}$ |
| 45° C. | 102.79 ± 7.62 | 18.10 ± 2.63 | 2462.15 ± 139.28 | 872.76 ± 57.50$^{a\#f}$ | 35.44$^{b}$ ± 0.94$^{beh}$ |
| 55° C. | 108.76 ± 5.36 | 17.24 ± 10.81 | 3853.07 ± 429.12 | 1528.36 ± 166.34$^{bd\#}$ | 39.67$^{d}$ ± 1.01$^{cf}$ |
| 65° C. | 107.89 ± 9.70 | 21.03 ± 6.34 | 3625.38 ± 989.41 | 1514.64 ± 394.85$^{cef}$ | 41.73 ± 3.52$^{dgh}$ |
| treatment effect | >0.05 | >0.05 | >0.05 | <0.0001 | <0.0001 |

LDd ANOVA using untransformed data

LDd – LDr ANOVA using untransformed data - (LDd removed from model as its effect was insignificant in the model (p > 0.05)

Zd Kruskal-Wallis test with pairwise comparisons using a Bonferroni correction

Zd – Zr ANCOVA using square root-transformed data with post hoc pairwise comparisons using a Sidak adjustment. Zd as a covariate retained in model as it had a highly significant effect (p < 0.0001).
$^{f}$p < 0.01;
$^{ad}$< 0.001;
$^{bce}$< 0.0001;
$^{\#}$p = 0.051 (bordering on significance).
Note:
25° C. vs 35° C. p = 0.071; 35° C. vs 45° C. p = 0.085 (approaching significance)
% R ANOVA using log-transformed data with post hoc Sidak multiple comparison tests. Zd as a covariate removed from model as it had an insignificant effect (p > 0.05).
$^{ae}$< 0.05;
$^{h}$< 0.01;
$^{bcdfg}$< 0.0001;
Note:
45° C. vs 55° C. p = 0.065 (approaching significance)
Note
ANOVA gives same result as ANCOVA when covariate is removed.

binations of two or more of the individual features mentioned or evident from the text or drawings. All of these different combinations constitute various alternative aspects of the invention.

The invention will now be further described with reference to the following non-limiting examples.

EXAMPLES

Example 1

Effect of Temperature on Remineralisation of Enamel Subsurface Lesions. The aim of these experiments was to determine the effect of temperature on remineralisation of enamel subsurface lesions using an in vitro model.

Solutions were prepared using CPP-ACP, and optionally NaF, to produce 1.0% w/v CPP-ACP pH 5.5 or 1.0% w/v CPP-ACFP pH 5.5.

Five different temperatures tested: (i) 25° C., (ii) 35° C., (iii) 45° C., (iv) 55° C. and (v) 65° C.

Human tooth enamel demineralized subsurface lesions were prepared in third molar enamel blocks using the method of Reynolds (J. Dent. Res. 1997, 76(9):1587-95).

Half the blocks were kept as control and the other half blocks were remineralized by suspending them individually in the 1.0% CPP-ACP+725 ppm F for 14 days at five different temperatures (25, 35, 45, 55, and 65° C.).

Example 2

A method for producing high concentration liquid compositions comprising CPP-ACP or CPP-ACP with free fluoride is described below.

Stock solutions of 3.25M CaCl$_2$) and 1.25 M NaH$_2$PO$_4$ (pH 5.5) were added in approximately thirty aliquots to a 10-15% w/v tryptic digest of casein until just before precipitation or gelation (usually producing a final concentration of approximately 78 mM to 124 Ca$^{2+}$ and 48 to 76 mM inorganic phosphate). The solutions were added slowly (that is, less than approximately 1% volume addition per minute) with adequate mixing. An aliquot of the phosphate solution was added first, followed by an aliquot of the calcium solution. The bulk solution pH was maintained at 9.0 using 1 to 10 M NaOH with thorough mixing. The sodium hydroxide solution was added automatically by a pH stat with the addition of the hydroxide ions usually being after each addition of the calcium ions. After completion of the addition of the calcium ions, phosphate ions and hydroxide ions the solution was filtered through a 0.1 micron filter to concentrate 1-2 fold. The retentate was then washed with 1-2 volumes of water to remove salts and inactive (and bitter tasting) peptides. The CPP-ACP solutions prepared were then spray dried or freeze dried to produce a white powder. This dried powder was then added to water to form 20% to 75% w/v CPP-ACP solutions at pH 5.5 by addition of 1-10 M HCl, or with added NaF to produce 3260 ppm F for 25% w/v, 4890 ppm F for 38%, 6520 ppm F for 50% w/v, 8151 ppm F for 63% CPP-ACP and 9,880 ppm F for 75% CPP-ACP at pH 5.5.

The 75% w/v solution was prepared by adding 75 g CPP-ACP powder to 20 ml water with a small amount of powder each addition (0.5 g/min) while maintaining the pH at 5.5 by the addition of 10 M HCl. The solution was thoroughly mixed after each addition to ensure dispersion. A concentrated NaF (0.95 M) solution was added together with 10 M HCl to ensure that 52 mmol of F was finally added. The CPP-ACP powder, NaF and HCl were added over 2-3 hours with water to a final volume of 100 ml. This produced a very viscous solution of 75% w/v CPP-ACP, 9,880 ppm F at pH 5.5.

Example 3

Remineralisation by CPP-ACFP and CPP-ACP in vitro at high concentrations. The aim of these experiments was to compare remineralisation by CPP-ACP+fluoride (F) and CPP-ACP at high concentrations (e.g. 20% w/v, 25% w/v, 30% w/v, 38% w/v, 40% w/v, 50% w/v and 63% w/v).

Human tooth enamel demineralized subsurface lesions were prepared in third molar enamel blocks. Half the blocks were kept as control and the other half blocks were treated as below:

Each enamel sample was pre-treated with 1M NaOH (5 ml) for 5 min at 45° C. then wash with water for 10 sec/pat dry;

Remineralized by suspending them individually in one of the following remineralization solutions:

CPP-ACP+F liquid compositions at 25% w/v, 38% w/v, 50% w/v, and 63% w/v CPP-ACP; or CPP-ACP only (no fluoride) liquid compositions at 20% w/v, 30% w/v, 40% w/v, and 50% w/v CPP-ACP, for 4 hours at 45° C.

Fluoride content for CPP-ACP+F liquid compositions is as shown in Table 2, specifically 3,260 ppm F for 25% w/v, 4,890 ppm F for 38% w/v, 6,520 ppm F for 50% w/v and 8,151 ppm F for 63% w/v CPP-ACP, respectively.

Enamel block was removed and paired with its control for embedding, sectioning and transverse microradiography and densitometric image analysis to determine percent mineral content gain (% Remineralization).

The levels of enamel subsurface remineralisation in only 4 hours are the highest level of remineralisation reported in such a short exposure time and has been achieved by the novel preparation of the liquid compositions containing high concentration CPP-ACP(F) and the novel use of temperature to facilitate remineralisation.

Example 4

A method for producing high concentration liquid compositions comprising CPP-ACP or CPP-ACP with free fluoride is described below.

30 g of CPP-ACP powder (commercial Recaldent) was added to 19.5 g of a 20,000 ppm F (NaF) solution to which 0.5 g of an 11 M HCl solution was added to give the final weight 50 g (hence this final solution is a 60% w/w CPP-ACP with 7,800 ppm F at pH 7.8 or 75% w/v CPP-ACP containing 10,000 mg/L F at pH 7.8). With thorough stirring (around 30 min) a homogeneous very viscous but stable solution was prepared with a pH of 7.8. This solution was then degassed to remove trapped air bubbles by placing the solution under vacuum for 24 hours.

The viscous, stable and safe (neutral pH) solution is easy to apply in the dental surgery and is more concentrated so produces a better effect over a longer period of time. The composition is still in liquid form so can be applied to the dental surface with a microbrush.

TABLE 2

Results of Remineralisation by CPP-ACP + F and CPP-ACP in vitro at high concentrations.

| Treatment | LDd (μm) | ΔZd (vol. μm) | ΔZd − ΔZr (vol. μm) | % R |
|---|---|---|---|---|
| 25% w/v CPP-ACP + 3260 ppmF | 114.73 ± 8.80 | 3021.30 ± 578.92 | 389.30 ± 71.06 | 13.05 ± 2.09 |
| 20% w/v CPP-ACP | 102.51 ± 6.30 | 2826.42 ± 349.81 | 234.83 ± 59.38 | 8.30 ± 2.24 |
| 38% w/v CPP-ACP + 4890 ppmF | 102.04 ± 9.06 | 2692.09 ± 448.70 | 515.01 ± 121.81 | 18.92 ± 2.27 |
| 30% w/v CPP-ACP | 104.02 ± 9.48 | 3041.59 ± 536.66 | 438.07 ± 65.16 | 14.43 ± 1.28 |
| 50% w/v CPP-ACP + 6520 ppmF | 112.45 ± 7.76 | 3145.51 ± 534.90 | 822.27 ± 181.33 | 25.81 ± 1.42 |
| 40% w/v CPP-ACP | 99.24 ± 6.87 | 2794.54 ± 501.81 | 458.38 ± 63.67 | 16.34 ± 1.47 |
| 63% w/v CPP-ACP + 8151 ppmF | 118.05 ± 10.67 | 3139.87 ± 218.49 | 859.84 ± 115.10 | 27.21 ± 2.14 |
| 50% w/v CPP-ACP | 104.00 ± 7.79 | 2691.53 ± 745.94 | 375.62 ± 129.73 | 13.98 ± 3.72 |

The invention claimed is:

1. A liquid composition comprising from greater than or equal to 40% w/v to less than or equal to 75% w/v stabilized amorphous calcium phosphate (ACP) and/or stabilized amorphous calcium fluoride phosphate (ACFP).

2. The liquid composition according to claim 1, wherein the composition further comprises fluoride.

3. The liquid composition according to claim 1, wherein the composition comprises greater than or equal to 45% w/v stabilized ACP and/or stabilized ACFP.

4. The liquid composition according to claim 1, wherein the stabilized ACP and/or stabilized ACFP is phosphopeptide stabilized.

5. The liquid composition according to claim 4, wherein the phosphopeptide is a casein phosphopeptide.

6. The liquid composition according to claim 1, wherein the composition comprises greater than or equal to 50% w/v stabilized ACP and/or stabilized ACFP.

7. The liquid composition according to claim 1, wherein the composition comprises greater than or equal to 55% w/v stabilized ACP and/or stabilized ACFP.

8. The liquid composition according to claim 1, wherein the composition comprises greater than or equal to 60% w/v stabilized ACP and/or stabilized ACFP.

9. The liquid composition according to claim 1, wherein the composition comprises greater than or equal to 65% w/v stabilized ACP and/or stabilized ACFP.

10. The liquid composition according to claim 1, wherein the composition comprises greater than or equal to 70% w/v stabilized ACP and/or stabilized ACFP.

11. A method for preparing a liquid composition comprising from greater than or equal to 40% w/v to less than or equal to 75% w/v stabilized amorphous calcium phosphate (ACP) and/or stabilized amorphous calcium fluoride phosphate (ACFP), comprising adding powder comprising stabilized ACP and/or stabilized ACFP at a rate of about 0.5 g/min to a solvent while maintaining pH below 7, wherein the powder and solvent are thoroughly mixed after each addition of powder.

12. The method according to claim 11, wherein the pH is maintained at or below about 5.5.

13. The method according to claim 11, wherein the pH is maintained with HCl.

14. The method according to claim 11, wherein the stabilized ACP and/or stabilized ACFP is phosphopeptide stabilized.

15. The method according to claim 14, wherein the phosphopeptide is a casein phosphopeptide.

16. A liquid composition comprising from greater than or equal to 40% w/v to less than or equal to 75% w/v stabilized amorphous calcium phosphate (ACP) and/or stabilized amorphous calcium fluoride phosphate (ACFP) prepared by the method of claim 11.

17. A method of mineralizing a dental surface or subsurface comprising contacting the dental surface or subsurface with a liquid composition comprising from greater than or equal to 40% w/v to less than or equal to 75% w/v stabilized amorphous calcium phosphate (ACP) and/or stabilized amorphous calcium fluoride phosphate (ACFP).

18. The method according to claim 17, wherein the method further comprises simultaneously or subsequently heating the dental surface or subsurface to which the liquid composition has been, or is being, applied to a temperature greater than 37° C.

19. The method according to claim 18, wherein the method comprises heating the dental surface or subsurface to which the stabilized ACP and/or stabilized ACFP has been, or is being, applied to a temperature greater than or equal to 40° C.

20. The method according to claim 17, wherein the liquid composition comprises greater than or equal to 45% w/v stabilized ACP and/or stabilized ACFP.

21. The method according to claim 17, wherein the stabilized ACP and/or stabilized ACFP is phosphopeptide stabilized.

22. The method according to claim 21, wherein the phosphopeptide is a casein phosphopeptide.

23. The method according to claim 17, wherein the dental surface or subsurface is a fluorotic lesion, or is a white spot lesion, or is a caries lesion, or is a lesion caused by erosion.

* * * * *